United States Patent
Pompon et al.

(10) Patent No.: US 8,211,676 B2
(45) Date of Patent: Jul. 3, 2012

(54) CHOLESTEROL-PRODUCING YEAST STRAINS AND USES THEREOF

(75) Inventors: Denis Pompon, Gif sur Yvette (FR); Bruno Dumas, Massy (FR); Roberto Spagnoli, Paris (FR)

(73) Assignee: Aventis Pharma S.A., Antony (FR)

( * ) Notice: Subject to any disclaimer, the term of this patent is extended or adjusted under 35 U.S.C. 154(b) by 970 days.

(21) Appl. No.: 11/568,572

(22) PCT Filed: May 2, 2005

(86) PCT No.: PCT/FR2005/001090
§ 371 (c)(1), (2), (4) Date: May 27, 2009

(87) PCT Pub. No.: WO2005/121315
PCT Pub. Date: Dec. 22, 2005

(65) Prior Publication Data
US 2009/0239837 A1    Sep. 24, 2009

(30) Foreign Application Priority Data
May 6, 2004    (FR) .................................. 04 04890

(51) Int. Cl.
C12P 7/02       (2006.01)
C12N 9/00       (2006.01)
C12N 1/20       (2006.01)
C12N 15/00      (2006.01)
C07H 21/04      (2006.01)

(52) U.S. Cl. .................. 435/155; 435/183; 435/252.3; 435/320.1

(58) Field of Classification Search .................. None
See application file for complete search history.

(56) References Cited

FOREIGN PATENT DOCUMENTS
| EP | 0727489 | 8/1996 |
|---|---|---|
| JP | 2004 141125 | 5/2004 |
| WO | WO9940203 | 8/1999 |
| WO | WO02061109 | 8/2002 |

OTHER PUBLICATIONS

Bae et al. J Biol Chem. May 21, 1999;274(21):14624-31.*
Skaggs et al. Gene. Feb. 22, 1996;169(1):105-9.*
Baudin-Baillieu et al., Construction of a Yeast Strain Deleted for the TRP1 Promoter and Coding Region that Enhances the Efficiency of the Polymerase Chain Reaction-Disruption Method, Yeast, vol. 13, 1997, pp. 353-356.
Bonneaud et al., A Family of Low and High Copy Replicative, Integrative and Single-Stranded *S. cerevisiae/E. coli* Shuttle Vectors, Yeast, vol. 7, 1991, pp. 609-615.
Duport et al., Self-sufficient biosynthesis of pregnenolone and progesterone in engineered yeast, Nature Biotechnology, vol. 16, No. 2, Feb. 1, 1998, pp. 186-189.
Lecain et al., Cloning by Metabolic Interference in Yeast and Enzymatic Characterization of *Arabidopsis thaliana* Sterol 7-Reductase, J. of Bio. Chem., vol. 271, No. 18, May 3, 1996, pp. 10866-10873.
Moebius et al., Molecular cloning and expression of the human delta7-sterol reductase, PNAS, vol. 95, No. 4, Feb. 17, 1998, pp. 1899-1902.
McCorkindale et al., A Comparison of the Types of Sterol Found in Species of the Saprolegniales and Leptomitales With Those Found in Some Other Phycomycetes, Phytochemistry, vol. 8, No. 5, 1969, pp. 861-867.
Ostlund et al., Cholesterol as a tracer for studes in cholesterol metabolism in humans, J. of Lipid Research, vol. 34, No. 10, 1993, pp. 1825-1831.
Soo-Han et al., Cholesterol biosynthesis from lanosterol: Molecular cloning, tissue distribution, expression chromosomal localization and regulation of rat 7-dehydrocholesterol reductase, a Smith-Lemli-Optiz syndrome related protein, J. of Biological Chemistry, vol. 274, No. 21, May 21, 1999, pp. 14624-14631.
Taton et al., Identification of a V5,7-Sterol-V7-Reductase in Higher Plant Microsomes, Biochem and Biophys Res Comm, vol. 181, No. 1, Nov. 27, 1991, pp. 465-473.
Waterham et al., Mutations in the 3Beta-Hydroxysterol V24-Reductase Gene Cause Desmosterolosis, an Autosomal Recessive Distorder of Cholesterol Biosynthesis, Am J. Hum. Genet, vol. 69, 2001, pp. 685-694.
Xu et al., Biosynthesis of Cholesterol in the Yeast Mutant ERG6, Biochemical and Biophysical Research Communications, vol. 155, No. 1, 1998, pp. 509-517.
S. Sturley, Conservation of eukaryotic sterol homeostasis: new insights from studies in budding yeast, Biochimica et Biophysica Acta 1529, 2000, pp. 155-163.

* cited by examiner

*Primary Examiner* — Christian Fronda

(57) ABSTRACT

The invention concerns the production of cholesterol in organisms of the Fungi kingdom. More particularly, the invention concerns genetically modified Fungus independently producing cholesterol from a simple carbon source. The invention also concerns the use of the inventive Fungus for producing non-marked and marked cholesterol.

17 Claims, 13 Drawing Sheets

Figure 1:
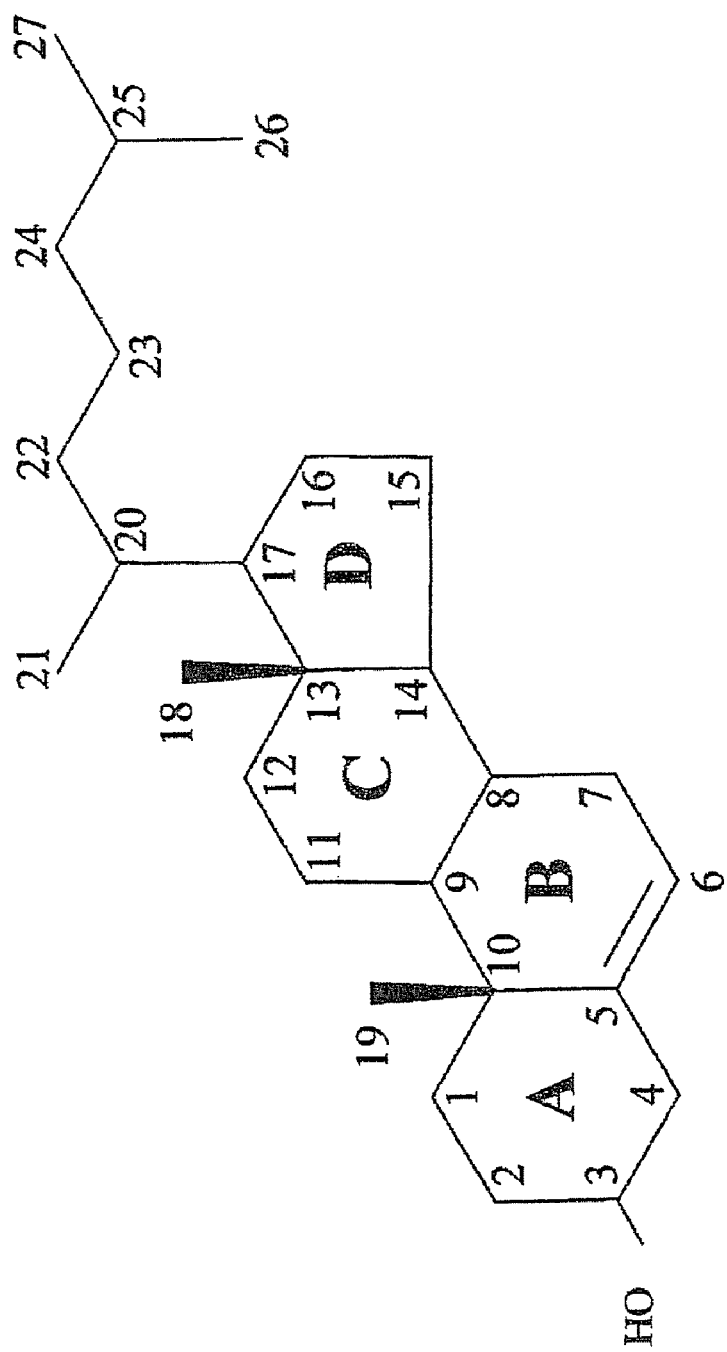

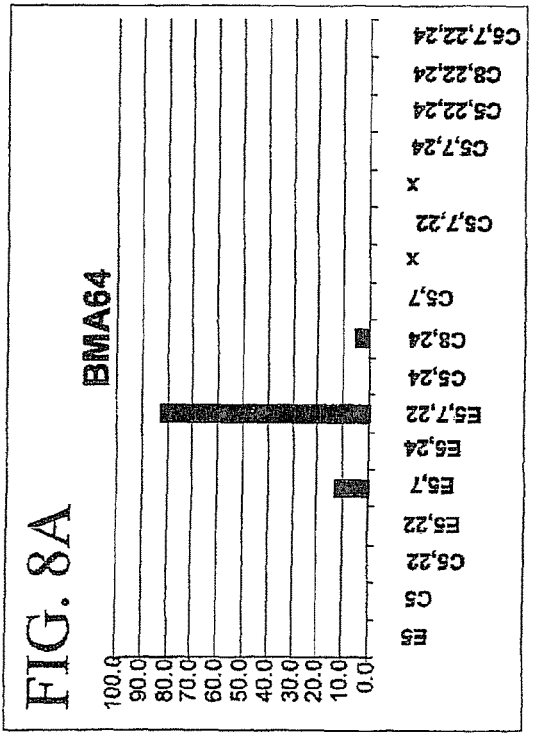
FIG. 8A BMA64
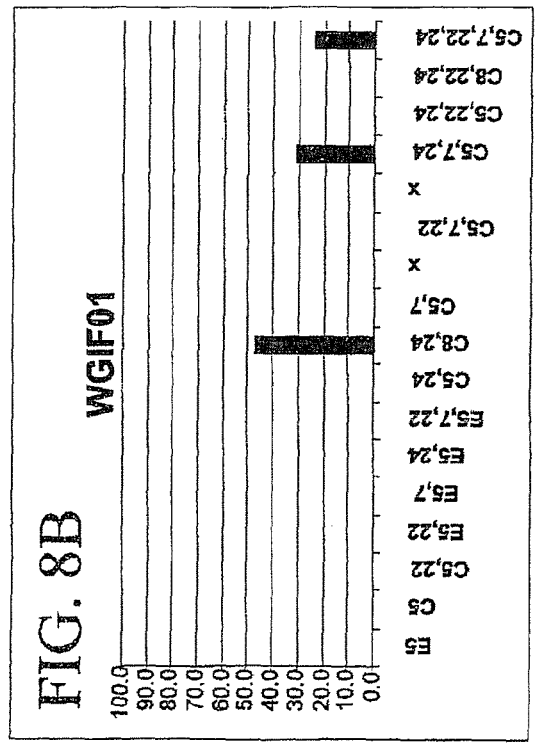
FIG. 8B WGIF01
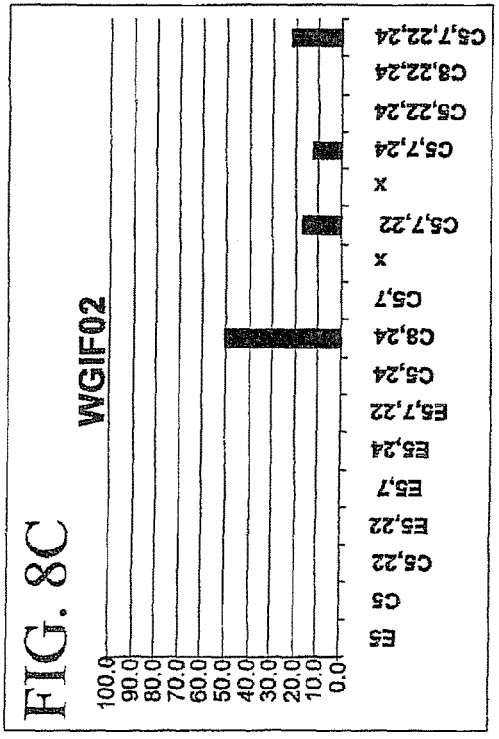
FIG. 8C WGIF02
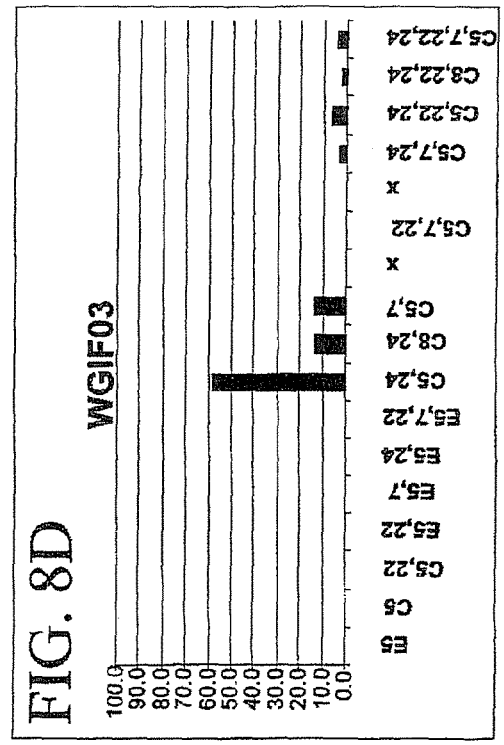
FIG. 8D WGIF03

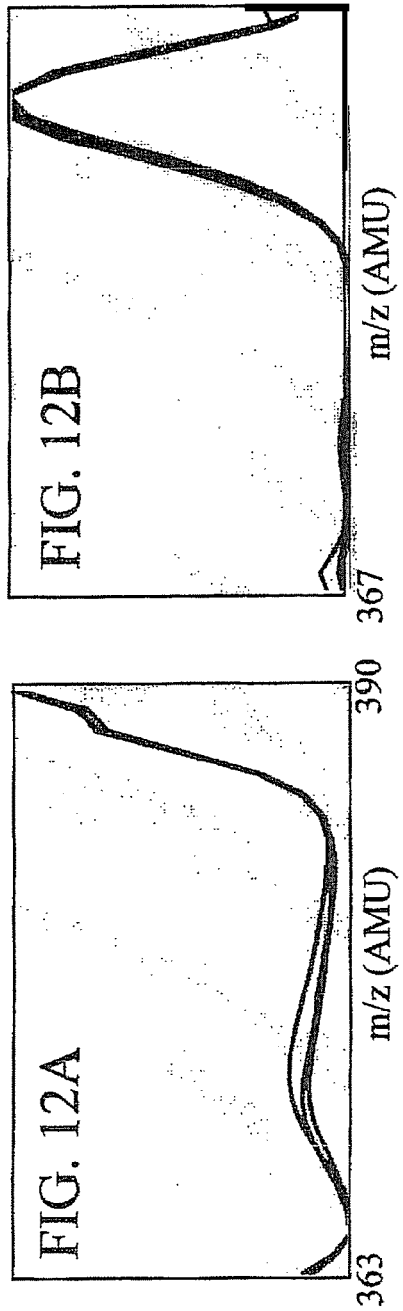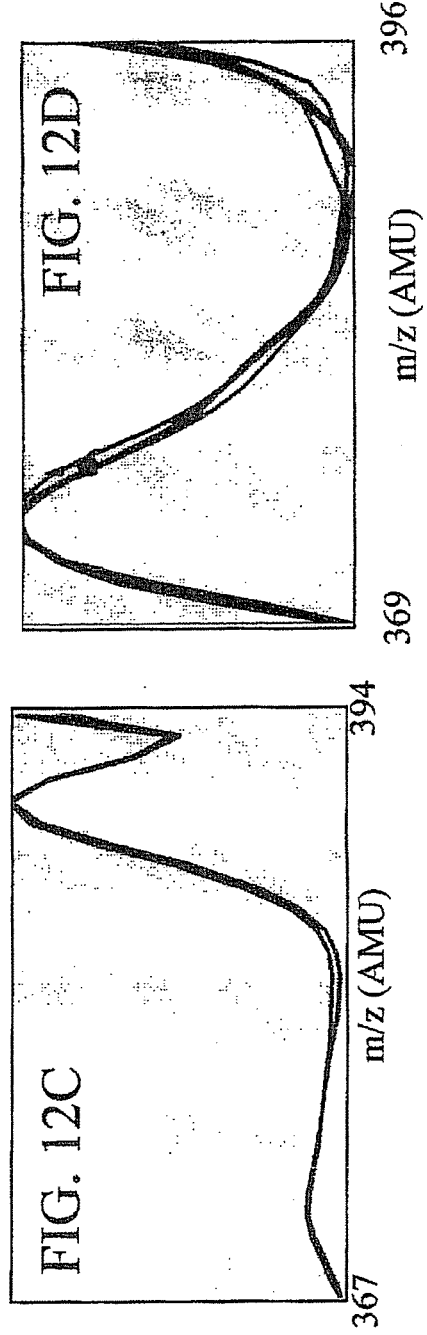
FIG. 12 ns of the kingdom Fungi.

SEQUENCE LISTING

<160> NUMBER OF SEQ ID NOS: 7

<210> SEQ ID NO 1
<211> LENGTH: 63
<212> TYPE: DNA
<213> ORGANISM: Artificial
<220> FEATURE:
<223> OTHER INFORMATION: OERG6trp1

<400> SEQUENCE: 1
cctagcgacg aaaagcatca ttggagtgaa taacttggac ttaccattct tagcattttg    60
acg                                                                  63

<210> SEQ ID NO 2
<211> LENGTH: 68
<212> TYPE: DNA
<213> ORGANISM: Artificial
<220> FEATURE:
<223> OTHER INFORMATION: OERG6trp2

<400> SEQUENCE: 2
gcataagagt gaaacagaat tgagaaaaag acaggcccaa ttcaaattcg ggtcgaaaaa    60
agaaaagg                                                             68

<210> SEQ ID NO 3
<211> LENGTH: 25
<212> TYPE: DNA
<213> ORGANISM: Artificial
<220> FEATURE:
<223> OTHER INFORMATION: OERG6trp3

<400> SEQUENCE: 3
agggccgaac aaagccccga tcttc                                          25

<210> SEQ ID NO 4
<211> LENGTH: 21
<212> TYPE: DNA
<213> ORGANISM: Artificial
<220> FEATURE:
<223> OTHER INFORMATION: OERG6trp4

<400> SEQUENCE: 4
ggcaaaccga ggaactcttg g                                              21

<210> SEQ ID NO 5
<211> LENGTH: 36
<212> TYPE: DNA
<213> ORGANISM: Artificial
<220> FEATURE:
<223> OTHER INFORMATION: OSA72

<400> SEQUENCE: 5
tatatagcgg ccgctttcgc tgattaatta ccccag                              36

<210> SEQ ID NO 6
<211> LENGTH: 34
<212> TYPE: DNA
<213> ORGANISM: Artificial
<220> FEATURE:
<223> OTHER INFORMATION: OSA77

<400> SEQUENCE: 6
tatatagcgg ccgcgagaag tgacgcaagc atca                                34

```
<210> SEQ ID NO 7
<211> LENGTH: 270
<212> TYPE: DNA
<213> ORGANISM: Artificial
<220> FEATURE:
<223> OTHER INFORMATION: modified sequence corresponding to the
      terminal NH2 of DHCR24 reductase

<400> SEQUENCE: 7
tagcgtggat ggccaggcaa ctttagtgct gacacataca ggcatatata tatgtgtgcg        60
acgacacatg atcatatggc atgcatgtgc tctgtatgta tataaaactc ttgttttctt       120
cttttctcta aatattcttt ccttatacat taggtccttt gtagcataaa ttactatact       180
tctatagaca cgcaaacaca aaggaattga caagtttgta caaaaaagca ggctaaaaaa       240
tggaacctgc cgtgtcgctg gccgtgtgcg                                         270
```

CHOLESTEROL-PRODUCING YEAST STRAINS AND USES THEREOF

CROSS REFERENCE TO RELATED APPLICATIONS

This application is a §371 National Filing of International Patent Application No. PCT/FR2005/001090, filed May 2, 2005, which claims priority under 35 U.S.C. §119(a) to French Patent Application No, 04/04,890, filed on May 6, 2004, the disclosures of which are incorporated herein in their entirety.

The present invention relates to the production of cholesterol in organisms of the kingdom Fungi.

Cholesterol (cf. FIG. 1) is the most important animal sterol. It is a fundamental component of cell membranes, of which it controls the fluidity, and is present in all animal tissues and particularly in nervous tissue.

Cholesterol is a product of considerable industrial interest. Thus, it is commonly used in the cosmetics industry. It is also used in the pharmaceutical industry, for example in drug delivery, and also in cell culture.

Cholesterol is also used in the industrial synthesis of vitamin $D_3$. This vitamin is subsequently used to supplement human food (in dairy products, for example) and animal food. Cholesterol is also advantageously used as an additive in animal food, in particular in food intended for farmed shrimp.

Currently, the vast majority of cholesterol that is marketed is extracted from animal tissue (a tiny amount is produced by chemical synthesis). Two major starting sources are used for the extraction of cholesterol: spinal cord from cattle and lanolin, which is the natural fat of sheep's wool.

The use of animal tissue as a starting product raises problems. Thus, the recent problems associated with transmission of the prion responsible for sheep scrapie to cattle (disease called BSE (bovine spongiform encephalitis) in cattle) have recalled the need for care when using animal tissue as a starting material. However, despite the steps taken, the risk of transmission of a pathogenic agent cannot be totally excluded. It would therefore be extremely advantageous to have a source of cholesterol that does not come from an animal tissue.

The aim of the present invention is to provide an abundant source of cholesterol that is safe from a health point of view. The inventors have shown, surprisingly, that it is possible to divert the natural production of ergosterol in Fungi so as to produce cholesterol.

GENERAL DESCRIPTION OF THE INVENTION

A first aspect of the invention concerns an organism of the kingdom Fungi that autonomously produces cholesterol.

A second aspect of the invention concerns an organism of the kingdom Fungi as defined above, wherein the latter is genetically modified.

A third aspect of the invention concerns an organism of the kingdom Fungi as defined above, wherein the latter produces cholesterol from a simple carbon source.

The invention also relates to an organism of the kingdom Fungi as defined above, expressing the 7-dehydrocholesterol reductase and 3β-hydroxysterol Δ24-reductase enzymes. More particularly, the invention relates to an organism as defined above, in which the sterol 24-C-methyltransferase enzyme has been inactivated and/or the C-22 sterol desaturase enzyme has been inactivated.

Another aspect of the invention concerns an organism of the kingdom Fungi as defined above, wherein the expression of the 7-dehydrocholesterol reductase and 3β-hydroxysterol Δ24-reductase enzymes is obtained by transformation of the organism.

The invention also relates to an organism of the kingdom Fungi as defined above, wherein the inactivation of the sterol 24-C-methyltransferase enzyme is carried out by gene inactivation and/or the inactivation of the C-22 sterol desaturase enzyme is carried out by gene inactivation.

Another aspect of the invention concerns an organism of the kingdom Fungi as defined above, which is chosen from the phylum Ascomycetes, more particularly from the subphylum Saccharomycotina, even more particularly from the class Saccharomycetes or Schizosaccharomycetes, even more particularly from the order Saccharomycetales or Schizosaccharomycetales, even more particularly from the family Saccharomycetaceae or Schizosaccharomycetaceae, even more particularly from the genus *Saccharomyces* or *Schizosaccharomyces*.

Another aspect of the invention concerns an organism of the kingdom Fungi as defined above, which is a yeast of the species *Saccharomyces cerevisiae* or *Schizosaccharomyces pombe*.

The invention also relates to a method for producing cholesterol of nonanimal origin, comprising the culturing of an organism as defined above. More particularly, in this method, the step consisting in culturing the organism is followed by a step consisting in extracting the cholesterol. Preferably, the extraction of the cholesterol is carried out with a non-water-miscible solvent.

More particularly, in the method as defined above, a saponification step is carried out before the extraction of the cholesterol. Even more particularly, in the method as defined above, a step consisting in mechanical grinding of the cells is carried out before the saponification or the extraction of the cholesterol.

Another aspect of the invention concerns the use of an organism of the kingdom Fungi as defined above, for producing cholesterol, or one of its metabolic intermediates, or a mixture of sterols, labeled with $^{13}C$ or with $^{14}C$ The invention also relates to a method for producing cholesterol, or one of its metabolic intermediates, or a mixture of sterols, labeled with $^{13}C$ or with $^{14}C$, comprising the following steps:
culturing an organism of the kingdom Fungi as defined above on a $^{13}C$-labeled or $^{14}C$-labeled substrate, and
extracting said cholesterol, or one of its metabolic intermediates, or the mixture of sterols.

The invention also relates to a method for producing an isotopic mixture of cholesterol, of cholesterol intermediates or of cholesterol metabolites, labeled at various positions using isotope labels, comprising culturing an organism of the kingdom Fungi as defined above on a labeled substrate and then on an unlabeled substrate, the culture times on each of these substrates being chosen in order to obtain a defined isotope profile. The invention also relates to a sample of molecules of cholesterol, of cholesterol intermediates or of cholesterol metabolites labeled at various positions using isotope labels, that has a defined isotope profile and that can be obtained by means of this method of production.

The invention also relates to a composition containing, as a traceability label, an isotopic mixture of cholesterol, of cholesterol intermediates or of cholesterol metabolites, labeled at various positions using isotope labels and having a defined isotope profile. More particularly, this composition is intended for the field of human or animal food or therapy.

DETAILED DESCRIPTION OF THE INVENTION

The present invention relates to the production of cholesterol in organisms of the kingdom Fungi. In Fungi, no cholesterol is found in the natural state, the latter being an animal sterol. The major sterol of the cell membranes of these organisms is ergosterol.

The present invention makes it possible to perform cholesterol synthesis, through the multiplication of Fungi, in the presence of a simple carbon source. The method proposed by the present invention therefore makes it possible to obtain a large amount of cholesterol, at low cost, since the method uses the culturing of organisms of the kingdom Fungi and the addition of a simple carbon source, readily available commercially.

According to the present invention, the term "simple carbon source" is intended to mean carbon sources that can be used by those skilled in the art for the normal growth of a fungus and in particular of a yeast. It is intended to denote in particular the various assimilable sugars, such as glucose, galactose or sucrose, or molasses, or the by-products of these sugars. A simple carbon source that is most particularly preferred is ethanol and glycerol.

The fact that the production is carried out autonomously means that there is no need to add substrates in order to obtain the cholesterol, but that the organism can produce it only from the starting simple carbon source. It is also clear that the strain can produce the cholesterol using a substrate located upstream in the metabolic pathway, insofar as the strain of the organism according to the present invention contains all the genes required to complete the metabolic pathway for cholesterol production.

The invention relates in particular to a genetically modified organism of the kingdom Fungi (a Fungus) that autonomously produces cholesterol from a simple carbon source.

A certain number of genetic modifications of the fungus can be effected in order to divert the natural metabolic pathway of ergosterol production toward the production of cholesterol. The present invention thus relates to a genetically modified organism of the kingdom Fungi expressing the 7-dehydrocholesterol reductase and 3β-hydroxysterol Δ24-reductase enzymes. The strain of organism of the kingdom Fungi thus modified produces cholesterol. The Applicant has in fact been able to model, by virtue of the results obtained (cf. the example section of the present application), the metabolic pathway resulting in ergosterol and in some of its derivatives (cf. FIG. 2). Expression of the 7-dehydrocholesterol reductase and 3β-hydroxysterol Δ24-reductase enzymes in the fungus S. cerevisiae can allow the production of cholesterol by diverting part of the biosynthetic pathway for ergosterol.

The 7-dehydrocholesterol reductase enzyme bears the number EC: 1.3.1.21 in the International Enzyme Classification. It is also called delta-5,7-sterol-delta-7-reductase, 7-DHC reductase or Sterol delta-7-reductase, and will also be called Delta-7 sterol reductase, Delta-7Red, Delta 7 Reductase or Δ7-reductase in the remainder of this document. This enzyme catalyzes, in the natural state in plants, for example the NADPH-dependent reduction of delta-5,7-cholestadienol to delta-5-cholestaenol or the reduction of sterol intermediates having the double bond in the 7-8 position (Taton and Rahier, 1991). The gene encoding the 7-dehydrocholesterol reductase enzyme was isolated for the first time in the plant Arabidopsis thaliana; the isolation of the corresponding gene and the expression of this enzyme in the yeast Saccharomyces cerevisiae is described in patent EP 727 489. The sequences of this gene and of the protein are accessible under the following GenBank accession number: U49398 (Lecain et al., 1996).

A certain number of homologues of this gene have been described in other species. These are, for example, the homologous gene in humans (the nucleotide sequence of which is accessible under GenBank number AF034544, the protein sequence of which is accessible under GenBank number: AAC05086) (Moebius et al., 1998); the homologous gene in the rat Rattus norvegicus (the nucleotide sequence of which is accessible under GenBank number: AB016800, the protein sequence of which is accessible under GenBank number: BAA34306). Homologous genes have also been identified in the chicken Gallus gallus, with the Genbank reference BM490-402 or in the toad Xenopus laevis, with the Genbank reference BI315007, or the zebra fish Danio rerio, with the Genbank reference BQ132664. A gene encoding a delta7 sterol reductase activity is also found in plants such as rice, Oryza sativa, with the Genbank reference CA753545, or potato, Solarium tuberosum, with the Genbank reference BF342071. This gene encoding a delta7 sterol reductase activity can also be found in the protist Mastigamoeba balamuthi, with the Genbank reference BE636562.

Those skilled in the art will be able to readily isolate other homologous genes encoding the 7-dehydrocholesterol reductase enzyme in other organisms. They may in particular refer to the cloning method described in example 1 of patent EP 727 489, which describes a cloning method for isolating a cDNA encoding a protein having delta-5,7-sterol-delta-7-reductase activity. Those skilled in the art may also readily determine the 7-dehydrocholesterol reductase activity of the corresponding proteins, in particular using the activity assay also described in example 1 of patent EP 727 489.

Expression of the 7-dehydrocholesterol reductase enzyme in an organism of the kingdom Fungi according to the invention can be obtained by any means known to those skilled in the art. This may in particular involve transformation of the organism with a construct comprising an expression cassette consisting of a transcription promoter, preferably homologous, of the open reading frame encoding the 7-dehydrocholesterol reductase enzyme and of a suitable transcription terminator, according to the usual rules known to those skilled in the art. As homologous promoter, use will in general be made of a promoter that is suitable for allowing sufficient and functional expression of the heterologous protein. The promoter may, for example, be the PGK promoter, the ADH promoter, the CYC1 promoter, the GAL10/CYC1 promoter, the TDH3 promoter or the TPI promoter. The terminator may, for example, be the terminator of the phosphoglycerate kinase (PGK) gene. Said expression cassette can be integrated, in the form of one or more copies, into the nuclear or mitochondrial genome of the host, or can be carried by an artificial structure of the yeast artificial chromosome (YAC) type or be carried by an episomal genetic element such as a plasmid. In order to effect this type of expression, yeast of the Yarrowia lipolitica, Kluyveromyces lactis or Pichia pastoris type can, for example, be used.

Preferably, the 7-dehydrocholesterol reductase enzyme expressed is the enzyme of the plant Arabidopsis thaliana (an example of method of expression of this enzyme in the yeast Saccharomyces cerevisiae is described in patent EP 727 489). It may, however, be any homologous or nonhomologous, natural or artificial, enzyme exhibiting the same enzyme activity.

The 3β-hydroxysterol Δ24-reductase enzyme, also called DHCR24 or 24-dehydrocholesterol reductase, naturally catalyzes the reduction of desmosterol (cholesta-5,24-dienol) or of lanosterol derivatives having a double bond in the 24-25 position on the side chain (for example, 14-desmethyl-lanosterol, zymosterol or cholesta-7,24-dienol), which reduction is necessary for the biosynthesis of cholesterol in humans in particular (H R. Waterham et al., 2001). This enzyme will also be called delta 24-(25) sterol reductase, delta 24 sterol Reductase or Δ24-reductase in the remainder of this document.

The gene encoding the 3β-hydroxysterol Δ24-reductase enzyme was isolated for the first time in humans; the isolation of the corresponding gene and the expression of this enzyme in the yeast *Saccharomyces cerevisiae* is described in the publication H R. Waterham et al., 2001. The sequences of this gene and of the protein are accessible under the following GenBank accession numbers: NM_014762 and NP_055577.

A certain number of homologues of this gene have been described in other species. They are, for example, the homologous gene in mice (*Mus musculus*) (the nucleotide sequence of which is accessible under GenBank number: NM_053272, the protein sequence of which is accessible under GenBank number: NP_444502). Homologues have been described in the worm *Caenorhabditis elegans*, and in particular a complementary DNA with the Genbank reference AF026214. Homologous sequences have also been described in plants, such as cotton, *Gossypium hirsutum*, with the Genbank reference AAM 47602.1, rice, *Oryza sativa*, with the Genbank reference AAP53615, or pea, *Pisum sativum*, with Genbank reference AAK15493.

Those skilled in the art will be able to readily isolate other homologous genes encoding the 3β-hydroxysterol Δ24-reductase enzyme in other organisms. They may in particular refer to the cloning method described in the publication H R. Waterham et al., 2001. Those skilled in the art will also be able to readily determine the 3β-hydroxysterol Δ24-reductase activity of the corresponding proteins, in particular using the activity assay also described in the publication (Waterham et al., 2001).

Expression of the 3β-hydroxysterol Δ24-reductase enzyme in an organism of the kingdom Fungi according to the invention can be obtained by any means known to those skilled in the art. This may in particular involve the means described above with regard to the expression of the 7-dehydrocholesterol reductase enzyme.

Preferably, the 3β-hydroxysterol Δ24-reductase enzyme expressed is the human enzyme. An example of isolation of the corresponding gene and of expression of this enzyme in the yeast *Saccharomyces cerevisiae* is described in the publication H R. Waterham et al., 2001. It may, however, be any homologous or nonhomologous, natural or artificial, enzyme exhibiting the same enzyme activity.

Advantageously, the organisms of the kingdom Fungi according to the present invention express the 7-dehydrocholesterol reductase and 3β-hydroxysterol Δ24-reductase enzymes and also exhibit inactivation of the sterol 24-C-methyltransferase enzyme.

The sterol 24-C-methyltransferase enzyme bears the number EC-2.1.1.41 in the International Enzyme Classification. It is also called ERG6p, Delta(24)-methyltransferase, Delta (24)-sterol methyltransferase, Zymosterol-24-methyltransferase, S-adenosyl-4-methionine:sterol delta(24)-methyltransferase, SMT1, 24-sterol C-methyltransferase, S-adenosyl-L-methionine:delta(24(23))-sterol methyltransferase or Phytosterol methyltransferase. This enzyme naturally catalyzes the C-24 methylation of zymosterol, resulting in the formation of fecosterol.

The gene encoding the sterol 24-C-methyltransferase enzyme was named Erg6 in the yeast *Saccharomyces cerevisiae*. The sequence of this gene is accessible under the following GenBank accession number: NC_001145. The sequence of the corresponding protein is accessible under the following GenBank accession number: NP_013706 (Bowman et al., 1997), (Goffeau et al., 1996).

A certain number of homologues of this gene have been described in other Fungi. They are, for example, the homologous gene in *Schizosaccharomyces pombe* (the nucleotide sequence of which is accessible under GenBank number Z99759, the protein sequence of which is accessible under GenBank number: CAB16897) (Wood et al., 2002); the homologous gene in *Neurospora crassa* (the nucleotide sequence of which is accessible under GenBank number: NCB24P7, the protein sequence of which is accessible under GenBank number: CAB97289); the homologous gene in *Candida albicans* (the nucleotide sequence of which is accessible under GenBank number: AF031941, the protein sequence of which is accessible under GenBank number: AAC26626) (Jensen-Pergakes et al., 1998). Genes encoding an enzyme homologous to ERG6 have also been described in *Candida lusitaniae*, with Genbank reference AA021936.1 and also in *Pneumocystis carinii* (Kaneshiro et al., 2002) or in *Kluveromyces lactis* (Ozier-Kalogeropoulos et al., 1998).

Those skilled in the art will be able to readily isolate other genes homologous to the Erg6 gene in organisms of the kingdom Fungi. Those skilled in the art will also be able to readily determine the sterol 24-C-methyltransferase activity of the corresponding proteins, in particular using, as activity assay, the functional complementation of a yeast strain disrupted for these genes. The complementation is then attested to by the formation of sterols that are branched at the 24-position, in particular of sterols of ergosta-type carrying a methylene group at the 24-28 position. The presence of ERG6-type sterol 24-C-methyltransferase biological activity will also be determined in vitro by means of the techniques developed by (McCammon et al., 1984) or by Taylor and Parks (Taylor and Parks, 1978). Furthermore, the sterols produced and the substrate for the ERG6 enzyme will be separated by gas chromatography according to the technique developed by Nes in (Methods in Enzymology Steroids and Isoprenoids Volume 111 part B, 1985, "A comparison of Methods for the Identification of Sterols", pp. 3-37).

The strain of organism of the kingdom Fungi according to the present invention expressing the 7-dehydrocholesterol reductase and 3β-hydroxysterol Δ24-reductase enzymes and also exhibiting inactivation of the sterol 24-C-methyltransferase enzyme produces cholesterol. The Applicant has in fact been able to determine that, surprisingly, the inactivation of the sterol 24-C-methyltransferase enzyme blocks the biosynthetic pathway for ergosterol upstream, and allows increased production of cholesterol by the fungus strain (cf. the example section of the present application).

The 7-dehydrocholesterol reductase and 3β-hydroxysterol Δ24-reductase enzymes are expressed as described above.

The inactivation of the sterol 24-C-methyltransferase enzyme can be carried out by any means known to those skilled in the art. It may in particular involve the introduction, by mutagenesis, of a nonsense mutation, of an insertion or of a deletion that causes a change in the reading frame in the gene encoding said protein.

It may also involve the expression of an antisense RNA that is complementary to the messenger RNA encoding said protein, or the gene silencing system known to those skilled in the art as RNAi (small interfering RNA) and the associated enzyme systems if these do not naturally exist in the host. The mutagenesis can be effected in the coding sequence or in a noncoding sequence so as to render the encoded protein inactive or to prevent its expression or its translation. The mutagenesis can be effected in vitro or in situ, by suppression, substitution, deletion and/or addition of one or more bases in the gene under consideration, or by gene inactivation.

This may in particular involve the introduction of an exogenous DNA into the coding sequence or promoter sequence (for example an expression cassette with homologous promoter and/or terminator and a heterologous coding portion). The expression cassette advantageously allows the expression of a selection marker. It is also possible to modify the promoter of the gene in order to reduce the level of expression. For fungi, inactivation is also carried out by interruption of the coding sequence with the coding sequence of a heterologous or homologous marker gene. The main techniques for interrupting a gene from fungi are described in the article by Johnston et al., (2002) (Methods in Enzymology Volume 350 Edited by Christine Guthrie and Gerry Fink; "Gene Disruption"; M. Johnston, L. Riles, J. Hegemann, pp. 290-315).

Advantageously, the organisms of the kingdom Fungi according to the present invention express the 7-dehydrocholesterol reductase and 3β-hydroxysterol Δ24-reductase enzymes and also exhibit inactivation of the C-22 sterol desaturase enzyme.

The C-22 sterol desaturase enzyme is also called ERG5p, Cyp61, cytochrome p-45061 or sterol delta22-desaturase. This enzyme naturally catalyzes the conversion of ergosta-5,7,24(28)-trienol to ergosta-5,7,22,24(28)-tetraenol by adding a double bond at position C22 (cf. FIG. 2).

The gene encoding the C-22 sterol desaturase enzyme was named Erg5 in the yeast *Saccharomyces cerevisiae*. The sequence of this gene is accessible under the following GenBank accession number: U34636. The sequence of the corresponding protein is accessible under the following GenBank accession numbers: AAB06217 (Skaggs et al., 1996) or P54781 (Bowman et al., 1997).

A certain number of homologues of this gene have been described in other Fungi. They are, for example, the homologous gene in *Schizosaccharomyces pombe* (the nucleotide sequence of which is accessible under GenBank number Z98974, the protein sequence of which is accessible under GenBank number: CAB11640) (Wood et al., 2002); the homologous gene in *Symbiotaphrina buchneri* (the nucleotide sequence of which is accessible under GenBank number: AB086896, the protein sequence of which is accessible under GenBank number: BAC01142) (Noda and Koizumi, 2003); the homologous gene in *Symbiotaphrina kochii* (the nucleotide sequence of which is accessible under GenBank number: AB086890, the protein sequence of which is accessible under GenBank number: BAC01139) (Noda and Koizumi, 2003); the homologous gene in *Candida albicans* (the nucleotide sequence of which is accessible under GenBank number: AL033396, the protein sequence of which is accessible under GenBank number: CAA21953) (Tait et al., 1997). The ERG5 gene has also been described in *Candida lusitaniae*, with Genbank reference AAO48601.

Those skilled in the art will be able to readily isolate other genes homologous to the Erg5 gene in organisms of the kingdom Fungi. Those skilled in the art will also be able to readily determine the C-22 sterol desaturase activity of the corresponding proteins, in particular using the activity assay described by B. A. Skaggs et al., 1996. This activity may also be demonstrated by functional complementation of an *S. cerevisiae* yeast disrupted beforehand in the erg5 gene. This complementation will be attested to by the presence, in the complemented strain, of ergosta-5,7,22-trienol. The C22 sterol desaturase activity can be measured in vitro using the method described by Kelly and Baldwin et al., JBC (1997), after lysis of the yeast (Kelly et al., 1997).

The strain of organism of the kingdom Fungi according to the present invention expressing the 7-dehydrocholesterol reductase and 3β-hydroxysterol Δ24-reductase enzymes and also exhibiting inactivation of the C-22 sterol desaturase enzyme produces cholesterol. The Applicant has in fact been able to determine that the inactivation of the C-22 sterol desaturase enzyme advantageously blocks the conversion of cholesterol to cholesta-5,22-dienol and allows stabilization of the production of cholesterol (cf. the example section of the present application). This blockage also occurs at the level of the conversion of cholesta-5,7-dienol, a precursor of cholesterol, to cholesta-5,7,22-trienol, a precursor of cholesta-5,22-dienol. Surprisingly, the C-22 sterol desaturase enzyme in fact accepts cholesterol as a substrate, and converts it to cholesta-5,22-dienol. This parasitic reaction can be eliminated by inactivating the C-22 sterol desaturase enzyme, as the Applicant has been able to determine.

The expression of the 7-dehydrocholesterol reductase and 3β-hydroxysterol Δ24-reductase enzymes is carried out as described above. The inactivation of the C-22 sterol desaturase enzyme can be carried out by any means known to those skilled in the art. They may in particular be the methods described above with regard to the inactivation of the sterol 24-C-methyl-transferase enzyme.

Advantageously, the organisms of the kingdom Fungi according to the present invention express the 7-dehydrocholesterol reductase and 3β-hydroxysterol Δ24-reductase enzymes and also exhibit inactivation of the C-22 sterol desaturase enzyme and inactivation of the sterol 24-C-methyltransferase enzyme. These strains in fact exhibit the cumulative advantages of the two inactivations and are cholesterol-producing strains.

The expression of the 7-dehydrocholesterol reductase and 3β-hydroxysterol Δ24-reductase enzymes and the inactivation of the C-22 sterol desaturase and sterol 24-C-methyltransferase enzymes are carried out as described above.

In one embodiment, the cholesterol is present in the strain of organism according to the present invention in a proportion greater than 20%, preferably 35%, most preferably 50% or more of the total sterols produced by the strain according to the invention (in particular the synthesis intermediates).

Preferably, the organisms of the kingdom Fungi according to the present invention are chosen from the phylum Ascomycetes, more preferably they are chosen from the subphylum Saccharomycotina, even more preferably they are chosen from the class Saccharomycetes or Schizosaccharomycetes, even more preferably they are chosen from the order Saccharomycetales or Schizosaccharomycetales, even more preferably they are chosen from the family Saccharomycetaceae or Schizosaccharomycetaceae, even more preferably they are chosen from the genus *Saccharomyces* or *Schizosaccharomyces*, entirely preferably, the organisms of the kingdom Fungi according to the invention belong to the species *Saccharomyces cerevisiae* or *Schizosaccharomyces pombe*.

The present invention also relates to a method for producing cholesterol of nonanimal origin, comprising the following steps:
  an organism of the kingdom Fungi as defined above is cultured,
  the cholesterol produced by this organism is extracted.

The extraction is based on the treatment of the fungus with a solvent for cholesterol, preferably a non-water-miscible solvent. This treatment can preferably be combined with any method of mechanical grinding of the cells. More preferably, the fungus will be treated, before extraction with the solvent, with a saponification mixture intended to release the cholesterol possibly bound to other cellular components such as, in particular, fatty acids. This saponification mixture may consist of a base, for example aqueous ammonia, sodium hydroxide or potassium hydroxide, dissolved in water or, more preferably, in a water-miscible organic solvent such as, for example, methanol or ethanol, or a solvent-water mixture. The saponification may be carried out without or preferably with heating to a temperature of 60-120° C., at atmospheric pressure or at low pressure. The extraction with the non-water-miscible solvent may be replaced with a solid-phase extraction on a hydrophobic resin. A sterol extraction method is described by L. Parks et al., (1985) (Methods in Enzymology 111 Edited by L. Rilling, L. Parks, C. Bottema, R. Rodriguez and Thomas Lewis, pp. 333-339).

The crude cholesterol thus obtained may be purified by any methods known to those skilled in the art, in particular that described by Boselli E, Velazco V, Caboni Mf and Lercker G J, Chromatogr A. 2001 May 11; 917 (1-2):239-44.

Other methods may also be used, such as that described for the extraction of cholesterol from sheep's wool. Those skilled in the art may in particular refer to the methods described in U.S. Pat. No. 2,688,623 or U.S. Pat. No. 2,650,929, or in British patents GB690879, GB646227 or GB613778.

Another aspect of the invention concerns the use of the strains according to the present invention in order to obtain cholesterol or one of its metabolic intermediates, or a labeled mixture of sterols. The term "metabolic intermediate of cholesterol" is intended to mean in particular the sterols specified in FIG. 2. They may in particular be cholesta-8,24(25)-dienol, cholesta-7,24(25)-dienol, cholesta-5,7,24(25)-trienol, cholesta-5,24(25)-dienol or cholesta-5,22-dienol.

Figure 10:
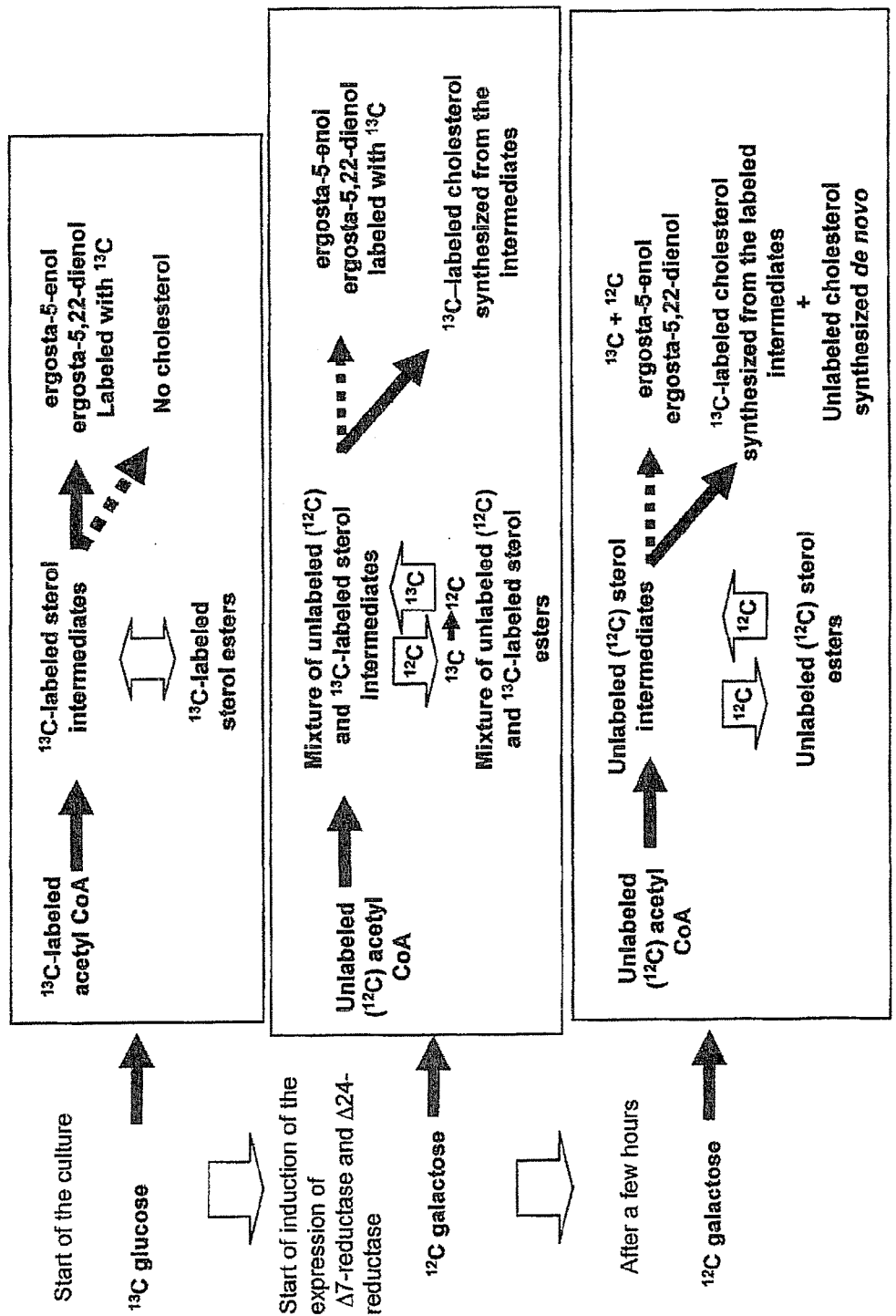

The principle for obtaining a labeled cholesterol is described in FIG. 10. This manipulation consists in first of all growing the fungus strain on a completely labeled substrate. The cells are then cultured on an unlabeled substrate. There is thus a change in isotope labeling of the carbon source; there ensues de novo synthesis of metabolic intermediates and then of sterol, including cholesterol, and comprising a gradual change in labeling. This therefore involves a profile that is complex but can be entirely experimentally determined, and that represents a unique isotope signature that depends at the same time:

1) on the labeling protocol and in particular on the culture times and conditions with labeled and unlabeled substrate,
2) on the precise genetic structure of the strain used,
3) on the precise time at which the cultures are stopped.

Once the culture has been stopped (for example by cell lysis or by stopping the culture in the presence of a sublethal concentration of cytotoxic or cytostatic antifungal products), the labeled cholesterol or one of its metabolic intermediates, or a labeled mixture of sterols, is extracted and purified as described above.

The isotope profile of the labeled cholesterol or of one of its metabolic intermediates, or of the labeled mixture of sterols, has several unique properties:

1) it can be modulated as desired by adjusting the culture conditions, the strain used and the sterol chosen. A unique label register can therefore be produced;
2) it is "combinable", i.e. several isotope signatures corresponding to several unique sterols labeled with isotope profiles that can themselves be modulated can be combined so as to form a "molecular alphabet";
3) it is reproducible and easy to determine experimentally;
4) it corresponds to a molecular tracer mixture that is easy to isolate, stable, colorless and odorless, nonvolatile and nontoxic, and that can be incorporated into foods, a medicinal product, additives or other products that can be assimilated by humans;
5) it cannot be falsified without having the specific recombinant strains and the very precise labeling, culturing and extraction conditions. In addition, knowledge of the isotope signature does not make it possible to track back to the parameters which made it possible to produce it.

Thus, an "isotope alphabet" for general use, that cannot be falsified and that can be incorporated into products of any type, including consumables, can be readily obtained by virtue of the present invention. There is a virtually unlimited number of "isotope words" that can be constituted from such an alphabet by making use of both the labeling profiles and the various types of sterols. The incorporation of such signatures into the most varied products therefore constitutes a unique method of labeling that cannot be falsified, unlike, for example, DNA signatures, which can be reproduced once they are known. The signature can, moreover, be read nondestructively, for example by laser ionization followed by mass spectrometry analysis (MALDI-TOF or the like).

The use of $^{13}$C-labeled substrate instead of the unlabeled carbon sources for culturing the fungus strains according to the invention makes it possible to synthesize very highly labeled sterols, and in particular cholesterol (comprising at least 95% of $^{13}$C carbon). The preparation of $^{14}$C radioactive sterols and cholesterol is also possible by the same approach. The method can also be incorporated into yeast strains that produce steroids, and in particular hydrocortisone (cf. patent application WO 02/061109), so as to produce $^{13}$C-labeled or $^{14}$C-labeled steroids, for example for RIA assays.

LEGEND FOR THE FIGURES

FIG. 1: Chemical formula of cholesterol, and also the nomenclature generally used for numbering the various carbons and the name of the various rings. The four rings of the cholesterol molecule are named A, B, C and D, respectively, and the carbons are numbered from 1 to 27.

Figure 2:
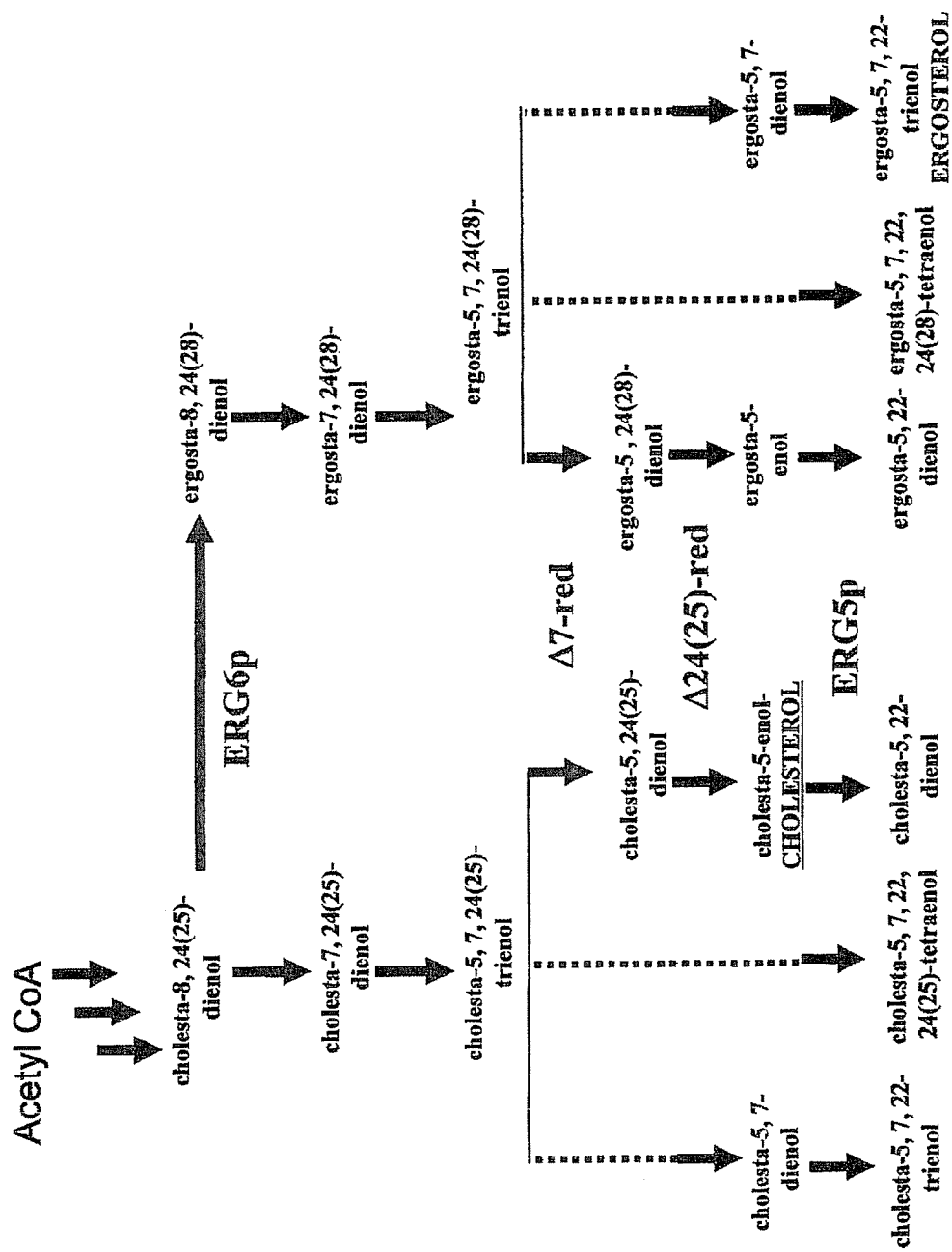

FIG. 2: Simplified scheme of the late portion of the biosynthetic pathway for sterols of the ergosta- and cholesta-types in natural or modified yeast. The scheme is not exhaustive, but makes it possible to define the steps involving the enzymes mentioned in this document. The ERG2p, ERG3p, ERG5p and ERG6p proteins are fungus or yeast proteins, whereas the Delta-7Red (Delta-7 sterol reductase) and Delta 24-(25)Red (Delta 24-(25) sterol reductase) proteins are heterologous proteins of mammalian origin or of plant origin.

Figure 3:
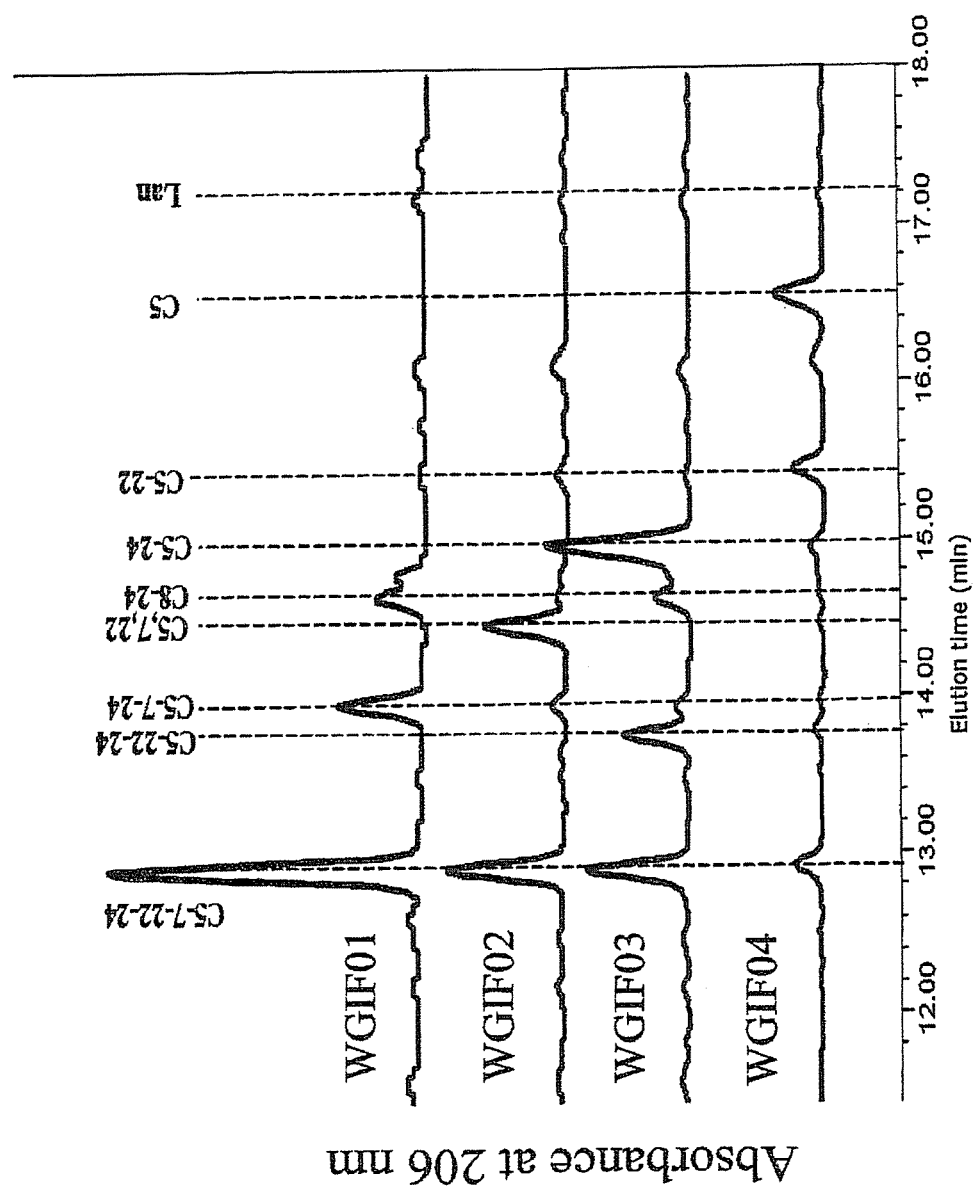

FIG. 3: Compared HPLC profile, with UV detection at 206 nm, of the free sterols of the strains derived from the BMA64 strain and identification of these sterols. The strains studied are as follows: WGIF01 (BMA64 strain disrupted in the erg6 gene (cf. example 1)), WGIF02 (BMA64 strain disrupted in the erg6 gene and expressing the Δ24-reductase, example 12), WGIF03 (BMA64 strain disrupted in the erg6 gene and expressing the Δ7-reductase, example 13), WGIF04 (BMA64 strain disrupted in the erg6 gene and expressing the Δ7-reductase and the Δ24-reductase, example 14). C5: cholesta-5-enol (cholesterol); C5,22: cholesta-5,22-dienol; C5,24: cholesta-5,24-dienol (desmosterol); C8,24: cholesta-8,24-dienol (zymosterol); C5,7,22: cholesta-5,7,22-trienol; C5,7,24: cholesta-5,7,24-trienol; C5,22,24: cholesta-5,22,24-trienol; C5,7,22,24: cholesta-5,7,22,24-tetraenol; lan: lanosterol.

Figure 4:
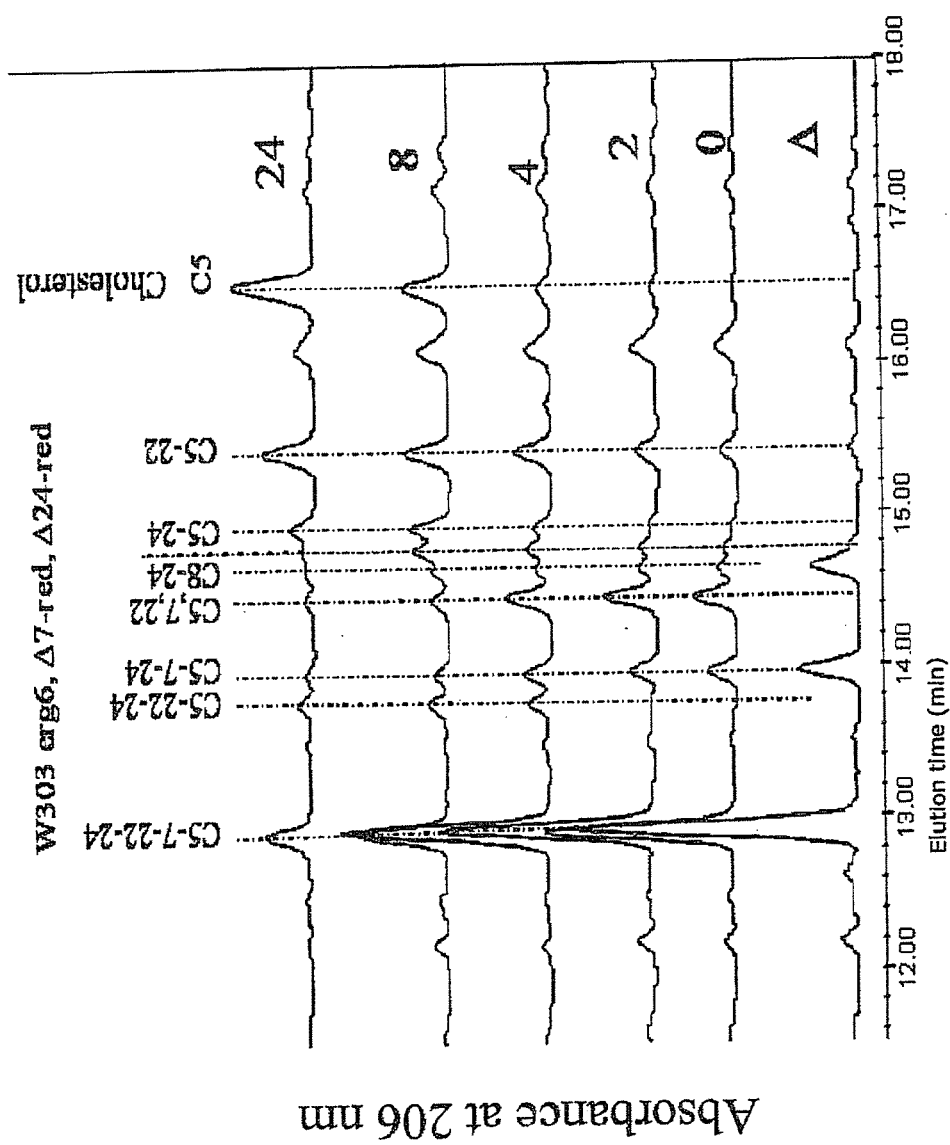

FIG. 4: Compared HPLC profile, with UV detection at 206 nm, of the free sterols of the WGIF04 strain (BMA64 strain disrupted in the erg6 gene and expressing the Δ7-reductase and the Δ24-reductase, example 14) after 0, 2, 4, 8 and 24 hours of induction with galactose. Δ: WGIF01 strain (example 1). For the WGIF04 strain, the samples are taken 0, 2, 4, 8 and 24 h after switching of the carbon source to galactose. The profile for the BMA64 strain bearing the erg6 disruption (WGIF01) presented is that obtained immediately after the switch to galactose. This profile remains virtually unchanged during the induction (0-24 h). The absorption signal at 206 nm corresponds to absorption coefficients that are variable from one sterol to the other. C5: cholesta-5-enol (cholesterol); C5,22: cholesta-5,22-dienol; C5,24: cholesta-5,24-dienol (desmosterol); C8,24: cholesta-8,24-dienol (zymosterol); C5,7,22: cholesta-5,7,22-trienol; C5,7,24: cholesta-5,7,24-trienol; C5,22,24: cholesta-5,22,24-trienol; C5,7,22,24: cholesta-5,7,22,24-tetraenol; lan: lanosterol.

Figure 5B:
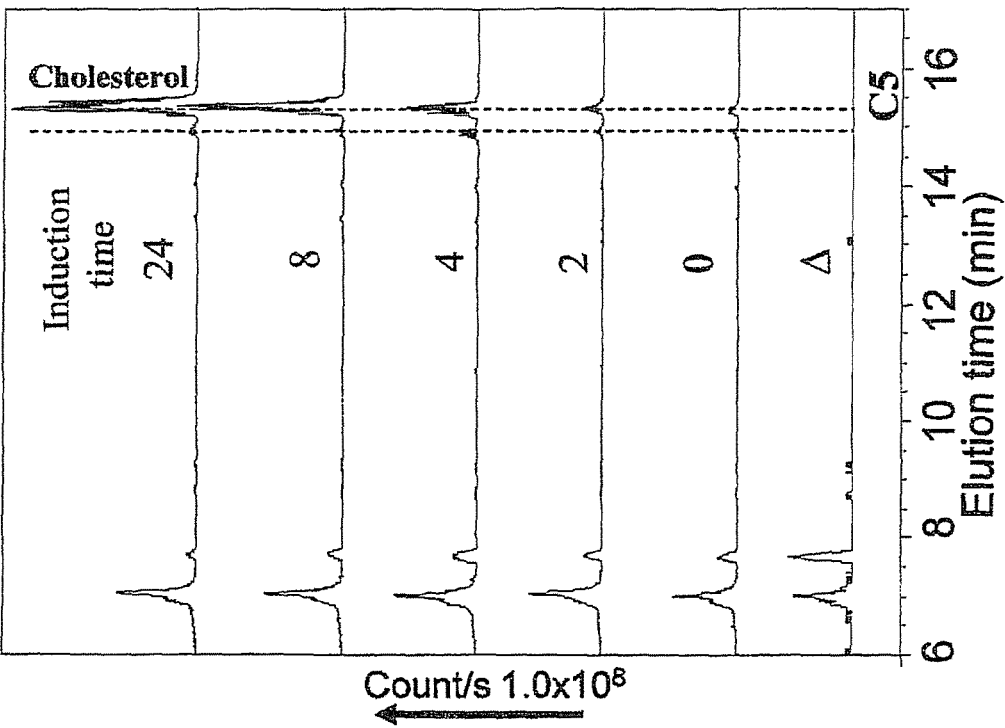

FIG. 5: Compared HPLC profile, with positive ionization electrospray detection (mass spectrometry), of the free sterols of the WGIF04 strain (example 14) after 0, 2, 4, 8 and 24 hours of induction with galactose. Δ: WGIF01 strain. C5: cholesta-5-enol (cholesterol); C5,22: cholesta-5,22-dienol; C5,24: cholesta-5,24-dienol (desmosterol); C8,24: cholesta-8,24-dienol (zymosterol). The HPLC profiles come from the same assays as those of FIG. 4.

Figure 5A:
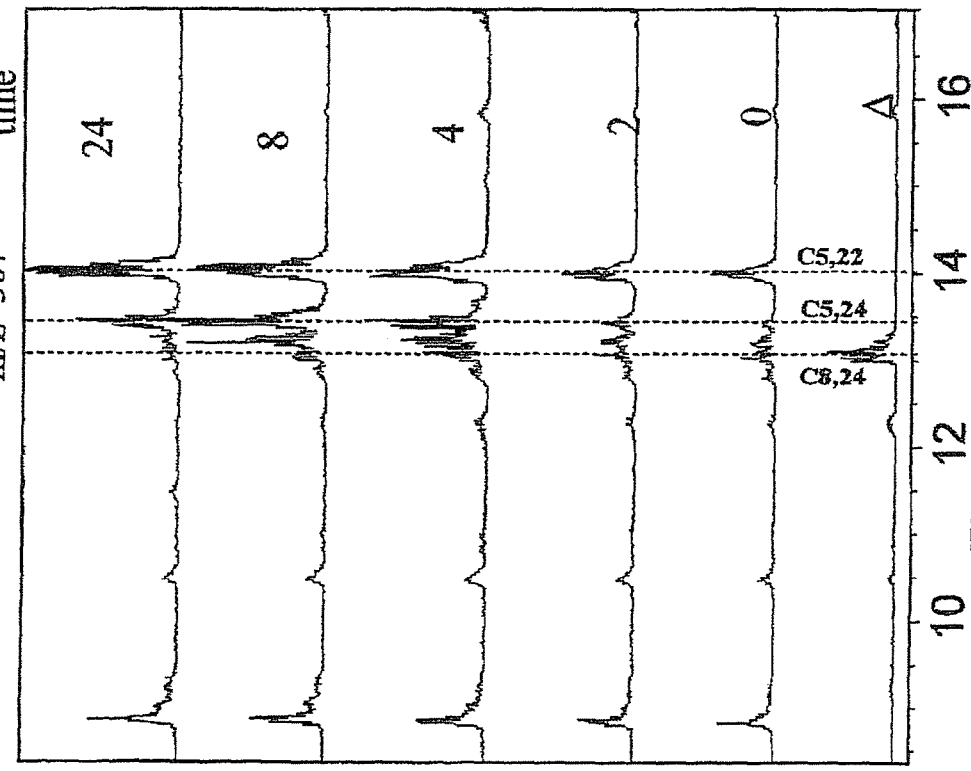

FIG. 5A (left): Detection at m/z=367, FIG. 5B (right): m/z=369.
y-axis: number of ions counted/second. x-axis: elution time in minutes.

Figure 6:
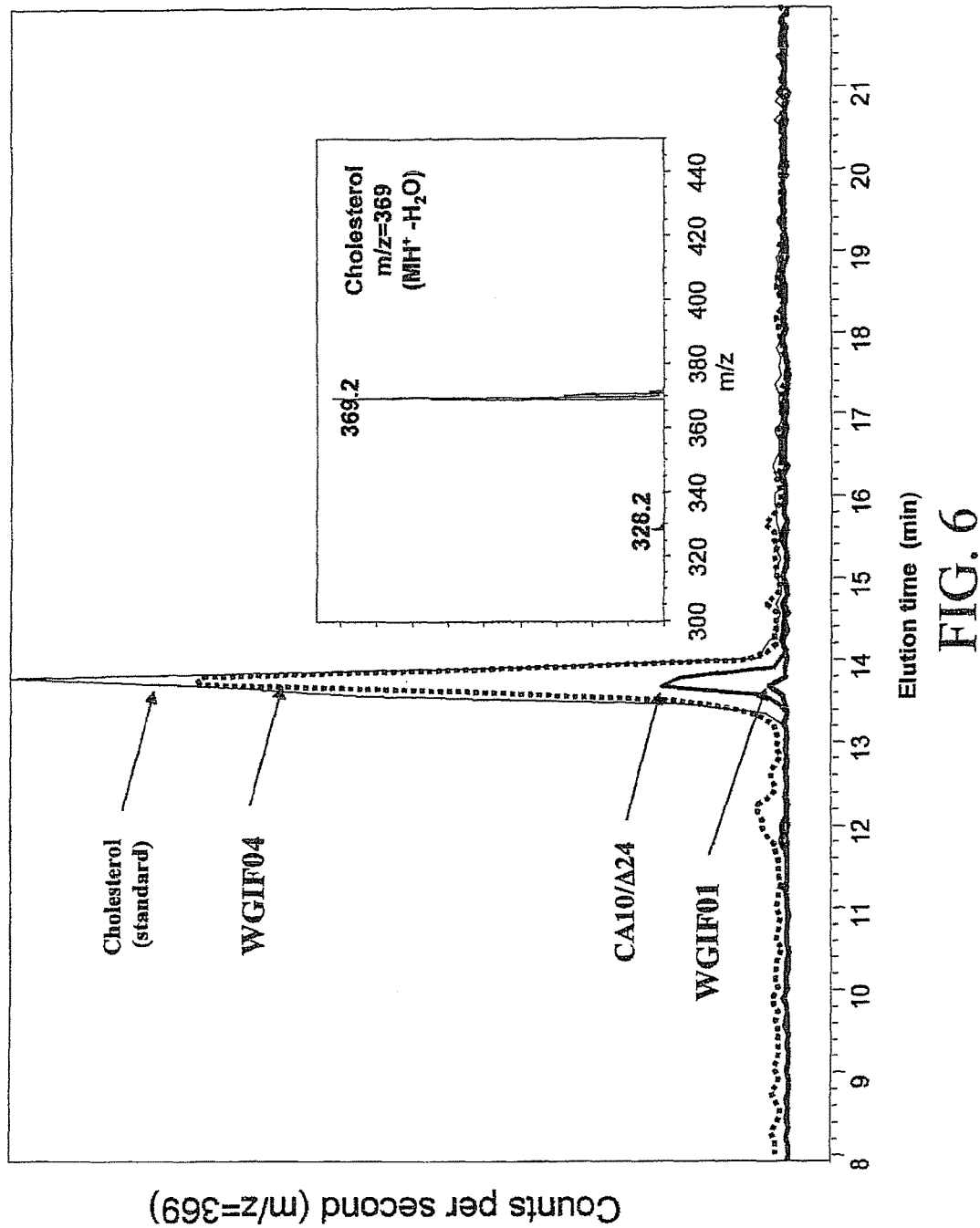

FIG. 6: Details of the profile at m/z=369 by HPLC for the three strains: WGIF01, CA10 bearing the expression plasmid for delta 24 sterol reductase, and for WGIF04, cholesterol is injected as an internal standard. The amounts of total sterols injected for the three strains correspond to extractions carried out on identical amounts of culture measured by the absorbance at 600 nm.

Figure 7:
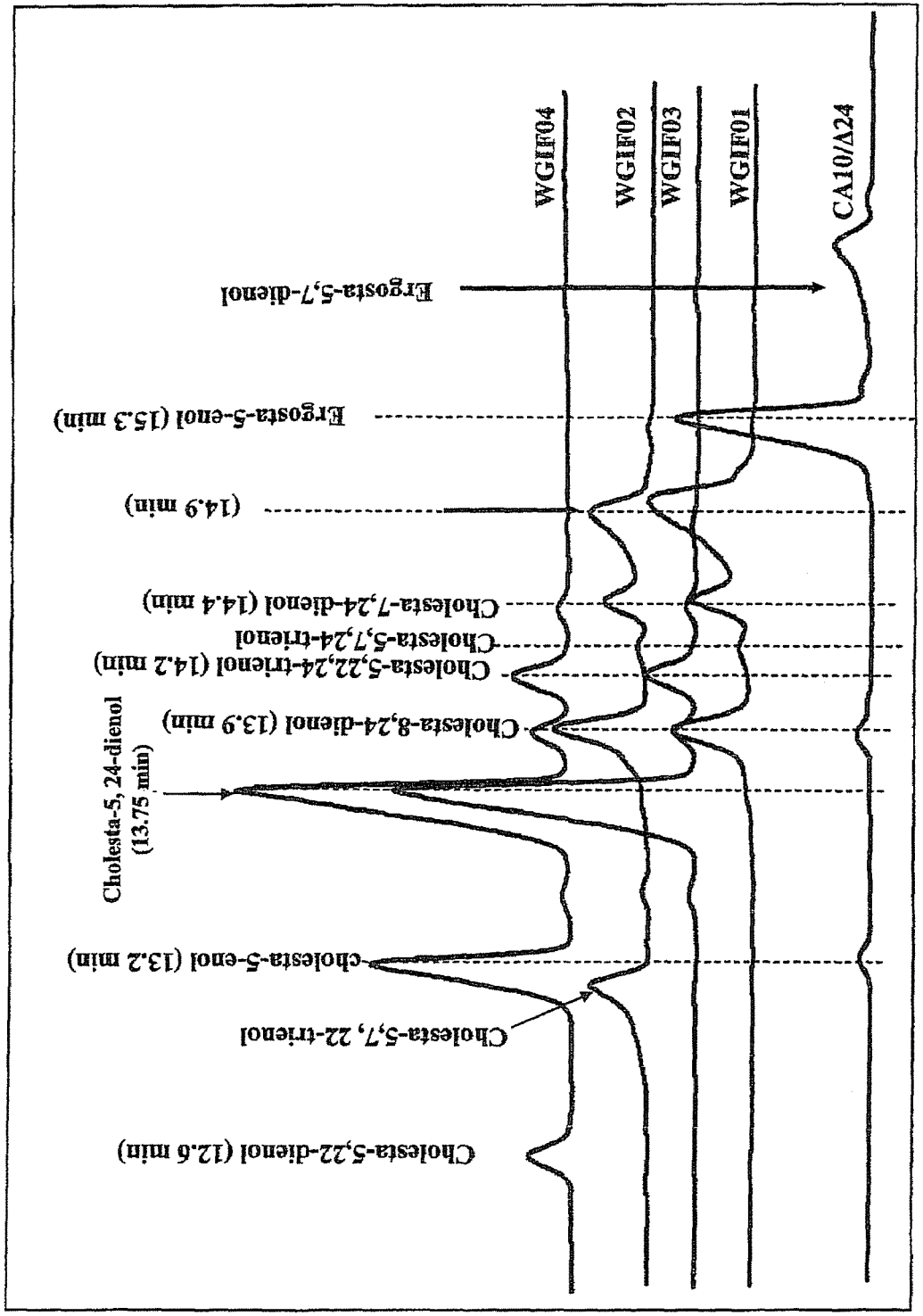

FIG. 7: Compared profiles of the total sterols (free and esters), by gas chromatography, of the WGIF01 (deletion of erg6), WGIF02 (deletion of erg6 with expression of the Δ24-reductase), WGIF03 (deletion of erg6 with expression of the Δ7-reductase), WGIF04 (deletion of erg6 with expression of the Δ24-reductase and A 7-reductase) and CA10 pYES_Delta24 (FY1679 genetic background, deletion of erg5 with expression of the Δ24-reductase, Δ7-reductase, erg5) strains. The response scales (flame ionization currents) are arbitrary. The profiles should only be compared qualitatively from one strain to the other. The retention time scale is, however, the same for all the strains (the retention times are expressed in minutes). The sterols are identified according to the criteria described in the present application.

FIG. 8: Quantitative distribution of the main free sterols in the yeast strains (BMA64 (FIG. 8A), WGIF01 (FIG. 8B), WGIF02 (FIG. 8C) and WGIF03 (FIG. 8D)) evaluated on the basis of the UV spectra. The distribution is given in % of the total species presented in the figure and which are the only ones that can be detected in appreciable amounts. In the absence of a standard for several of the intermediate sterols, the quantification is carried out on the basis of the UV spectra associated with each of the peaks of the HPLC chromatogram using the evaluated absorption coefficients given below (cf. table 1, the absorption coefficients are expressed in mM per liter and per cm.). To do this, the absorption coefficients corresponding to the unsaturated structural units present in the structure of a given sterol are sought in table 1 and optionally added (if several units are present in the same molecule) so as to provide an evaluation of the extinction coefficient of each type of sterol. The evaluation is done using the values at 280 nm if at least one unit that is absorbent at this wavelength is present, failing this, the wavelength 235 nm is used, and failing absorption at the latter wavelength, the wavelength 206 nm is used to evaluate the concentrations of each of the sterols from the respective absorption signals by HPLC.

Figure 9:
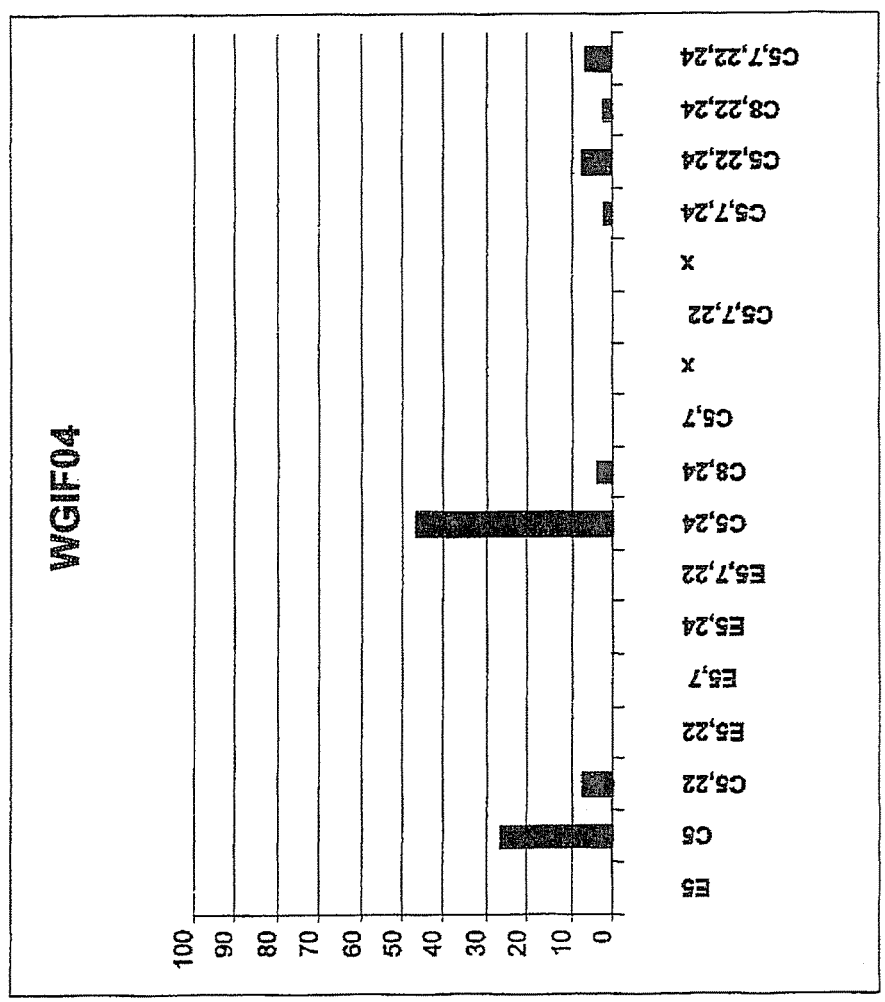

FIG. 9: Quantitative distribution of the main free sterols in the WGIF4 yeast strain, evaluated on the basis of the UV spectra. The quantifications are carried out in the same manner as described in FIG. 8.

FIG. 10: Principle of the isotope labeling of the sterols by substitution of carbon sources.

Figure 11:
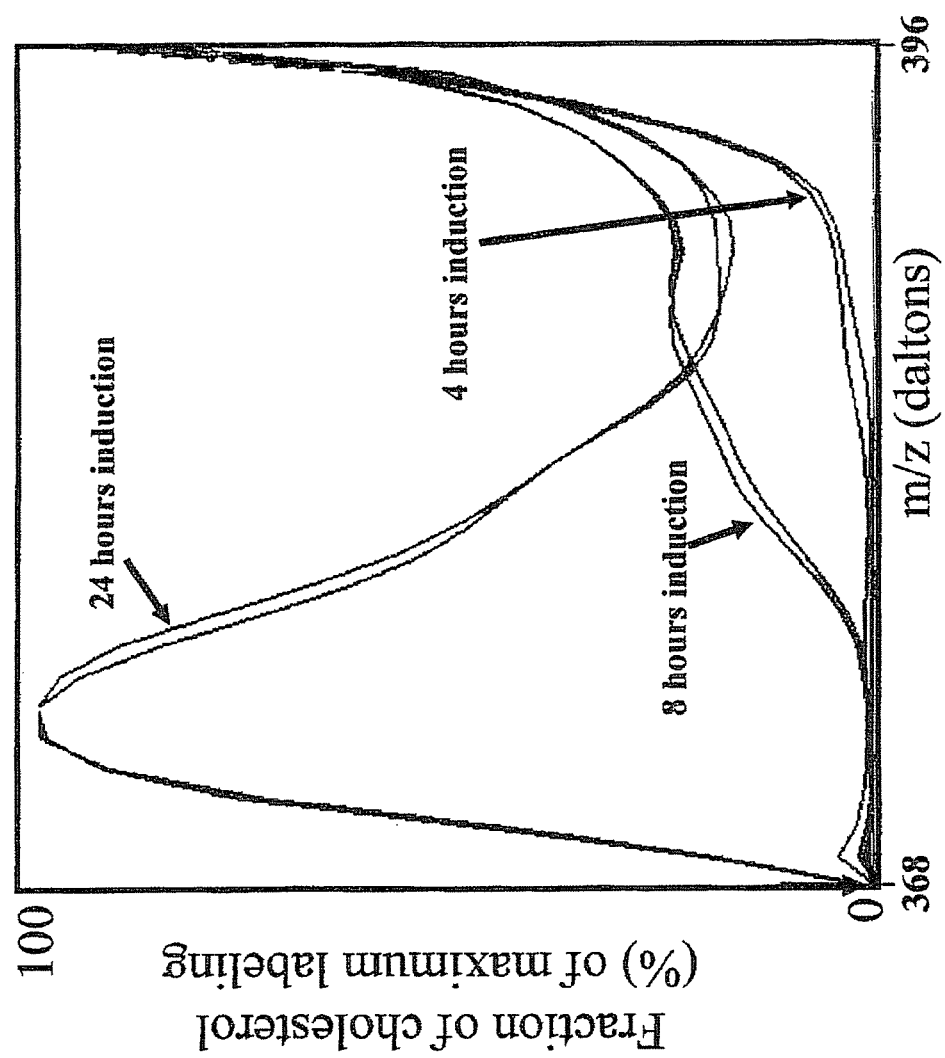

FIG. 11: Evaluation of the isotope labeling profiles for the cholesterol produced in the WGIF04 strain after 4, 8 and 24 hours of induction. The free sterols are extracted and separated by HPLC as described. A mass spectrum between the values of m/z 300 and m/z=450 is acquired every 0.2 seconds during the elution. These spectra are then averaged over windows of 1.8 seconds, and then subjected to a multilinear regression using, as regression base, a set of 24 vectors representing the theoretical mass distributions of the labeled cholesterol for a random incorporation, by independent selection, of the carbon 13 at each of the 27 positions of the molecule with a probability of labeling on each carbon that is variable between 0 and 1 according to the vector under consideration. The labeling probabilities for the various vectors used as base are chosen such that the cross-correlation coefficient for the distributions of two consecutive vectors of the base is 0.92, the base beginning with a vector corresponding to a probability of presence of 100% at all the positions on the carbon 12. The multilinear adjustment is made on the basis of a least square statistical criterion, nullifying the non-diagonal terms of the matrix of the products of 3 the partial derivatives of the Gauss method (maximum numerical filtering). After analysis, the mass spectra are then reconstructed on the optimized basis. The curves represented in the figures therefore represent the result of the optimal filtered reconstruction after standardization of the maximum amplitude at the value 100.

For each induction time, the two curves represent two independent profiles corresponding to elution times that differ by 1.8 seconds and corresponding to spectra located in the central zone of the cholesterol elution peak. The figure demonstrates that the analysis is highly reproducible.

FIG. 12: Example of various isotope signatures with various sterols or various induction times. The same calculation and representation as for FIG. 11, but for various sterols and various induction times. The value of RT indicates the range of retention time used for the calculation (in minutes). The values for this range are as follows:
FIG. 12 A: RT=12.25-12.42,
FIG. 12 B: RT=12.2-12.7,
FIG. 12 C: RT=12.25-12.35,
FIG. 12 D: RT=13.3-13.6.
The induction times are 8 or 24 hours.
The values of m/z indicate the left and right limits of the m/z values. The lowest value for m/z for each box corresponds to the m/z for the sterol made up entirely of carbon 12.

Figure 13:
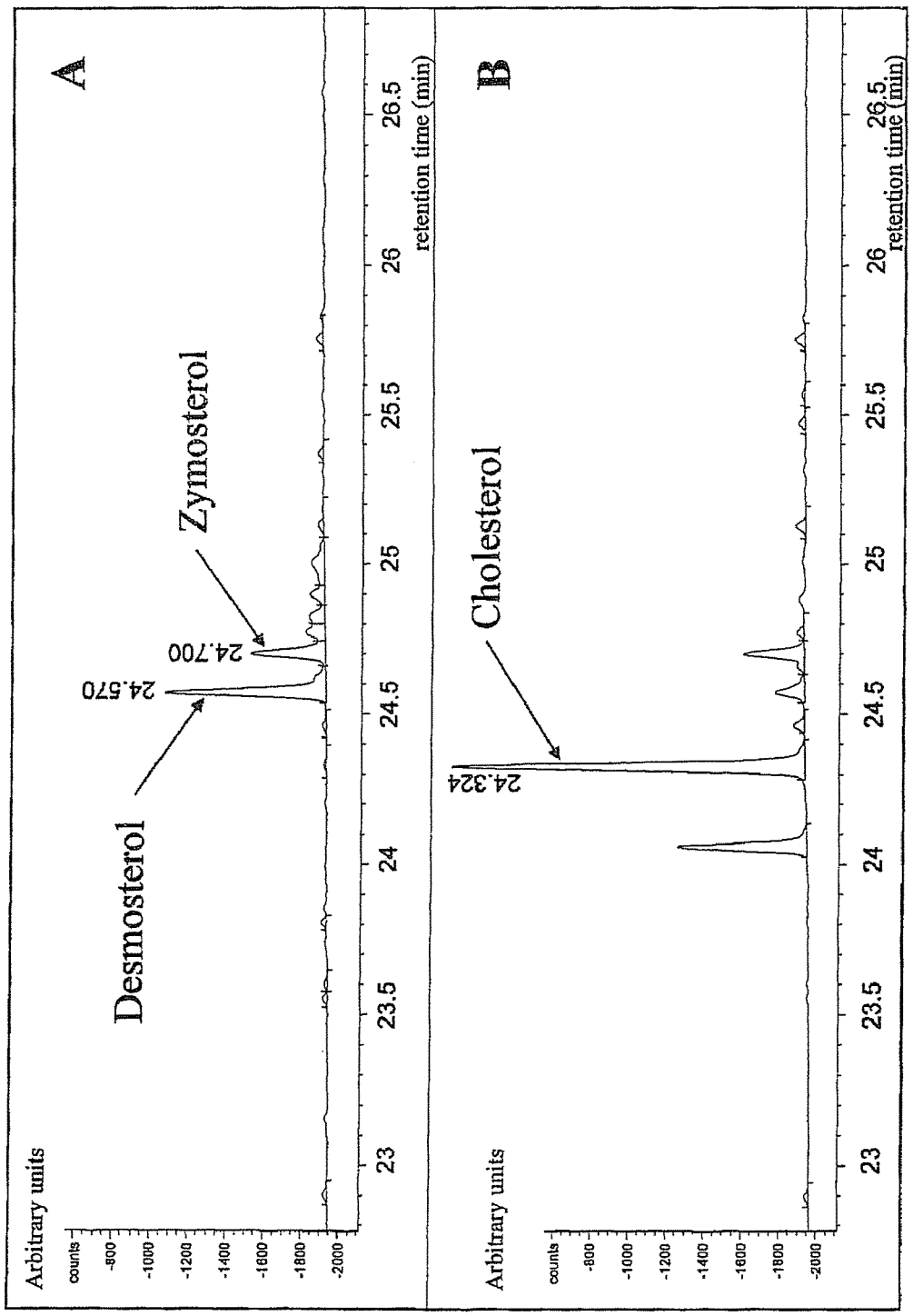

FIG. 13: Compared profiles of the total sterols (free and esters), in gas chromatography, of the YIM59/pIM303 strain (part A of the figure) and of the YIM59/pIM331 strain (part B of the figure) (cf. example 18). The response scales are arbitrary. The retention time scale is the same for both strains (the retention times are expressed in minutes). The sterols are identified according to the criteria described in the present application.

The present invention is illustrated using the following examples, which should be considered as nonlimiting illustrations.

The molecular biology techniques used are described by Ausubel et al., some yeast manipulations are described by Adams et al. (Adams and Holm, 1996).

EXAMPLE 1

Construction of an *S. cerevisiae* Yeast Strain with an Interruption in the Erg6 Gene (WGIF01 Strain)

The *S. cerevisiae* yeast strain WGIF01 in which the ERG6 gene is interrupted with the TRP1 gene was obtained by transforming the BM64 strain with a PCR product carrying a functional TRP1 gene bordered by extremities homologous to the ERG6 gene.

The BM64 strain (of genotype MATa; ura3-52; trp1Δ2; leu2-3_112; his3-11; ade2-1; can1-100) is a derivative of the *S. cerevisiae* yeast strain W303 MATα by complete deletion of the TRP1 gene. The BMA64 strain and the W303 MATα strain are described in the publication by Baudin-Baillieu et al. (Baudin-Baillieu et al., 1997).

To isolate the TRP1 gene, the TRP1 gene of the plasmid pFL44 (Bonneaud et al., 1991) was amplified using Z-TaqI (a DNA-dependent DNA polymerase) provided by the company Takara (PanVera LLC 501 Charmany Drive, Madison, Wis. 53719 USA). The pair of primers used makes it possible to amplify, by means of the DNA polymerase, the TRP1 gene bordered by sequences corresponding to the ERG6 gene.

The sequence of these primers is as follows:

```
                                            (SEQ ID No. 1)
OERG6trp1:
5'
(CCTAGCGACGAAAAGCATCATTGGAGTGAATAACTTGGACTTACCAttc
ttagcattttgacg) 3'.

(SEQ ID No. 2)
OERG6trp2:
5' 5'
(GCATAAGAGTGAAACAGAATTGAGAAAAAGACAGGCCCAATTCAaattc
gggtcgaaaaaagaaaagg) 3'.
```

The PCR (polymerase chain reaction) product thus obtained is purified by electroelution of the fragment corresponding to the expected size, and is used to transform the BM64 strain by the lithium chloride technique as described by (Gietz et al., 1995).

After transformation, the treated yeasts are plated out on a minimum medium containing no tryptophan (Gietz et al., 1995). 41 transformed BM64 colonies that are prototrophic for tryptophan are thus obtained. These 41 colonies are then tested for three of their properties: sensitivity to nystatin, genomic structure of the insertion of the TRP1 gene, and profile by gas chromatography of the total sterols that they produce.

For this, the 41 colonies are transferred onto a minimum medium containing, respectively, 10, 20 or 50 μg/ml of nystatin; about ten colonies are capable of growing on the medium containing a dose of 50 g/ml of nystatin. These resistant colonies are selected in order to verify their gene structure and also their sterol compositions.

The insertion of the TRP1 gene into the ERG6 gene is verified by PCR using a pair of oligonucleotides covering the junction between the functional TRP1 gene and the disrupted ERG6. This pair of oligonucleotides is as follows:

```
                             (SEQ ID No. 3)
OERG6trp3:  AGGGCCGAACAAAGCCCCGATCTTC
and (SEQ ID No. 4)
OERG6trp4:  GGCAAACCGAGGAACTCTTGG.
```

Some strains exhibit the expected PCR profile, i.e. a fragment of 800 base pairs corresponding to the size expected for a TRP1 insertion into ERG6.

With the aim of verifying that the ERG6 gene is indeed inactivated in these strains, an analysis of the sterol compositions of these strains by gas chromatography and by high pressure liquid chromatography was carried out (Duport et al., 2003; Szczebara et al., 2003).

These analyses confirm the absence of ergosterol synthesis and the accumulation of abnormal sterols compatible with the expected disruptions of the biosynthetic pathway in the disrupted strain.

One strain was more particularly selected, and called WGIF01.

EXAMPLE 2

Construction of the CA10, CA14 and CA23 Strains

The CA10 strain (of genotype: MATα, rho$^+$, GAL2, ura3-52, trp1-Δ63, his3-Δ200, erg5::HYGRO$^R$, ade2::GAL10/CYC1::Δ7Reductase::PGK1, LEU2::GAL10/CYC1::matADR::PGK1), the CA14 strain (of genotype: MATα, rho$^+$, GAL2, ura3-52, trp1-Δ63, his3-Δ200, erg5::HYGRO$^R$ atf2::G418$^R$, ade2::GAL10/CYC1::Δ7Reductase::PGK1, LEU2::GAL10/CYC1::matADR::PGK1), and the CA23 strain (of genotype: MATα, rho$^+$, GAL2, ura3-52, trp1-Δ63, his 3-Δ200, erg5::HYGRO$^R$, are1::G418$^R$, are2::HIS3, ade2::GAL10/CYC1::Δ7Reductase::PGK1, LEU2::GAL10/CYC1::matADR::PGK1), and also the constructions thereof, are described in the reference Duport et al., the technical content of which, regarding the construction of these strains is incorporated into the present application by way of reference.

These strains produce and contain, in their membranes, unnatural sterols (as described in European patent application EP 0727 489) and in particular ergosta-5-enol (campesterol).

These three strains do not express the product of the ERG5 gene, which is nonfunctional due to insertion into its coding sequence of the hygromycin resistance gene. In addition, these strains express the cDNA encoding plant Δ7 reductase (European patent application EP 0727 489 describes in particular the cloning of the Δ7 reductase of the plant *Arabidopsis thaliana*, which is incorporated into the present application by way of reference, the GenBank accession number of this sequence is ATU49398).

The CA14 strain is derived from the CA10 strain by disruption of the ATF2 gene. The product of this gene results in acetylation of pregnenolone on position 3 (as is described in patent application WO99/40203).

The CA23 strain is a strain derived from the CA10 strain by deletion of the ARE1 and ARE2 genes; the two proteins Are1p and Are2p are responsible for the esterification of ergosterol (Sturley, 2000) and possibly of cholesterol since they are homologous to the enzyme responsible for the esterification of cholesterol in mammals (ACAT).

EXAMPLE 3

Construction of the Plasmid for Expressing the Δ24-25 Reductase of Human Origin (Plasmid pYES_Delta24)

The construction of this plasmid was described by Waterham et al., 2001. The construction consisted in placing the cDNA encoding Delta 24 sterol reductase under the control of the pGAL1 promoter and of the tCYC1 terminator in the vector pYES2 (Invitrogen SARL, Cergy Pontoise, France). This plasmid is an *E. coli/S. cerevisiae* shuttle plasmid and contains a 2 micron origin of replication and a URA3 gene, allowing it to replicate in yeast and making it easy to select the yeast transformed with this plasmid.

In addition, the GAL1 promoter is galactose-inducible.

EXAMPLE 4

Construction of the Plasmid pAG1 Expressing *A. thaliana* Expressing Δ7-Reductase A plasmid was constructed specifically for the expression of *A. thaliana* Delta 7-reductase, on a single-copy vector. The plasmid pAM1 was used for this construction. This plasmid, the construction of which is described in PCT application WO 02/061109 (cf. example 9.b of said application, which is incorporated into the present application by way of reference), is an *E. coli/S. cerevisiae* shuttle plasmid based on an autonomous replication sequence and a centromere (ARS CEN). The selection marker is the ADE2 gene. This plasmid is compatible, and can therefore replicate at the same time as a plasmid based on a 2 micron origin of replication. This plasmid in particular has a unique NotI site for cloning expression cassettes, as described in the PCT application above.

This site was used to clone an *A. thaliana* Delta7-reductase expression cassette originating from the CA10 strain. In fact, this expression cassette is very effective and enables the CA10 strain, which is also disrupted for ERG5, to produce campesterol (ergosta-5-enol) as the major sterol (Duport et al., 1998). The genomic DNA fragment of the CA10 strain containing the delta7-reductase gene is amplified using the following primers:

```
                                          (SEQ ID No. 5)
OSA72 5' (TATATAGCGGCCGCTTTCGCTGATTAATTACCCCAG) 3'

(SEQ ID No. 6)
OSA 77 5' (TATATAGCGGCCGCGAGAAGTGACGCAAGCATCA) 3'.
```

The amplification is carried out on the genomic DNA of the CA10 strain prepared by the rapid phenol/chloroform extraction technique as described by Adams et al. (Adams and Holm, 1996).

Fifty nanograms of CA10 genomic DNA are used as matrix for amplification using the primers OSA72 and OSA77. The Taq DNA polymerase and the enzymatic conditions came from the company Stratagene. The amplification conditions were as follows: initial denaturation for 5 min at 95° C., then subsequently, thirty cycles were carried out consisting of a denaturation for 30 s at 95° C., a hybridization for 30 s at 50° C. and then an elongation for 1 min at 72° C. The reaction is terminated by a final extension for 10 min at 72° C.

The PCR fragment is then digested with the NotI enzyme and purified on agarose gel and then cloned conventionally into the unique NotI site of the plasmid pAM1. The plasmid thus obtained was named pAG1.

It is a single-copy vector for expressing *A. thaliana* Delta7-Reductase in yeast, the Delta7-Reductase gene being placed under the control of the GAL10/CYC1 promoter (Lecain et al., 1996).

EXAMPLE 5

Extraction of the Free and Esterified Sterols in the Yeast, for the Analyses

1) Conditions for Extracting the Free and Esterified Sterols in the Yeast (Procedure 1)
a) Conditions for extracting the free sterols:
The cell pellet is washed twice with 500 µl of deionized and filtered water, in a glass tube.

The cells are then resuspended in 500 µl of water containing 0.5 mm glass beads, corresponding to 150 µl of liquid in the tube.

An extraction is carried out twice with 2 ml of 1,2-dichloroethane with vigorous agitation on a vortex for 10 minutes. After the first extraction, the mixture of cells, glass beads and solvent is centrifuged for 5 minutes at 1500 g for the purpose of separating the two phases.

The two organic fractions derived from the two successive extractions are combined and dried under a stream of nitrogen for a few hours.

The sterol extract is suspended in 100 µl of acetonitrile in order for it to be analyzed by high performance liquid chromatography (HPLC) (Szczebara et al., 2003) or in 100 µl of hexane for the gas chromatography (GC) analyses (Duport et al., 2003).

b) Conditions for Extracting the Total Sterols: Saponification and Extraction of the Esterified Sterols, Qualitative Analysis Procedure 1:

The cell pellet is resuspended in 500 µl of purified water. 2 ml of potassium hydroxide KOH at 10% in methanol are added to this suspension. The mixture is heated for one hour at 60° C. in closed tubes. After the incubation, and once the tubes have returned to ambient temperature, the mixture is extracted three times with 2 ml of hexane. Between each extraction, the two phases are separated by centrifugation for 5 min at 1500 g. After each extraction, the organic phase is transferred into a new tube, and the three organic phases are then combined and then dried under a stream of nitrogen.

The sterol residue is resuspended in 100 µl of 100% acetonitrile in order for it to be analyzed by high performance liquid chromatography (HPLC) (Szczebara et al., 2003) or in 100 µl of hexane for the gas chromatography (GC) analyses (Duport et al., 2003).

2) Conditions for Extracting the Free and Esterified Sterols in the Yeast, for Qualitative Analysis (Procedure 2)

The strains are cultured in rich medium (10 g of bactopeptone per liter and 10 g of yeast extracts per liter) with 2% of glucose as carbon source in order to obtain 500 mg of lyophilized cells. These dried cells are taken up in 3 ml of methanol (100%) containing 1 g of KOH and a trace of pyrogallol, and the mixture is then incubated for 45 minutes at 90° C. After returning to ambient temperature, the sterols are extracted with 5 ml of hexane. The organic phase is separated into three samples having the same volume, and is dried under a stream of air. Two of the samples of the extracted sterols are taken up in 100 µl of hexane for the analyses by gas chromatography (GC) and gas chromatography/mass spectrometry GC/MS, and the third sample is taken up in 150 µl of methanol for the high performance liquid chromatography (HPLC) studies.

EXAMPLE 6

Analysis of the Free and Esterified Sterols in the Yeast by Gas Chromatography (GC)

1) Gas Chromatography (GC) with FID (Flame Ionization Detection)

The (free or total) sterol extract suspended in hexane is prepared according to procedure 1 (cf. example 5 1) a) and b)). An injection control is added to the sterol mixture, in general cholesterol at a concentration of 10 to 50 ng/µl.

From 1 to 3 µl of samples are then injected onto a gas chromatography device under the following conditions. 1 to 3 µl were injected onto an Alltech SE30-type column (column reference: 30 m×0.32 mm IDX 0.25/µm). The gas vector is helium. The Split ratio is between 50 and 80. The column head pressure is 30 psi. The injector is set at 280° C. The initial temperature of the column is 130° C. for 0.5 of a minute. It increases to 230° C. at a rate of 40° C./min, and then from 230° C. to 280° C. at a rate of 3° C./min. The column is then maintained at 290° C. The temperature of the detector is 310° C.

2) Gas Chromatography (GC) with FID (Flame Ionization Detection) Coupled with Mass Spectrometry (GC/MS)

The total sterol extract suspended in hexane is prepared according to procedure 2. The GC used is equipped with a conventional "split/splitless" injector with a conventional DB5 column that is meters in length and 0.25 mm in diameter.

The injection is carried out at 230° C. with helium as gas vector, at a flow rate of 2 ml/min. The column goes from 130 to 290° C. in 4 stages. The column is maintained at 130° C. before injection and then increases to 230° C. with a ramp of 40° C./min, then from 230° C. to 280° C. with a ramp of 3° C./min and then from 280° C. to 290° C. with a ramp of 30° C./min. The column remains at 290° C. for 5 minutes.

At the gas chromatography column outlet, the molecules are then analyzed by means of spray mass spectrometry in an ionization chamber such as that of a device of Turbo Mass type from Perkin Elmer. The molecules are fragmented with a high-energy electron beam. The various fragments are then separated on a quadrupole filter and then detected on an ion detector. A mass spectrum which includes the masses of all the products of fragmentation of the M+ ion corresponds to each mass located on the ion current graph. This mass spectrum obtained at a given retention time on the column is compared with libraries of fragmented products and also with those described for sterols by Quail and Kelly. (Methods in Molecular Biology Vol. 53 Yeast Protocols Edited by Evans; M. Quail and S. Kelly "The Extraction and Analysis of Sterols from Yeast" pp. 123-131 (1996)).

In this way, it was possible to demonstrate the effect of the deletion of the ERG6 gene in the WGIF01 strain and in particular the absence of ergosta-8,24(28)-dienol and the presence of sterol of the type cholesta having the double bond in the 24(25)-position.

EXAMPLE 7

Analysis of the Free and Esterified Sterols in the Yeast by High Performance Liquid Chromatography (HPLC) with UV Detection or Detection by Mass Spectrometry 1) Analysis by UV Detection HPLC:

Ten to 30 µl of the sterol extract (suspended in acetonitrile or methanol and prepared according to procedure 1 or 2 (cf. example 5)) are injected onto an X terra RP18 type 4.6×100 mm column (Waters, Milford, Mass. 01757 USA).

The separation is carried out on a gradient composed of water containing 0.02% of TFA (trifluoroacetic acid) (buffer A) and of pure acetonitrile (buffer B). The column is maintained at 60° C. during the analysis.

The HPLC device used is of the "Waters 600 E System Controller" type (Waters, Milford, Mass. 01757 USA). The UV detection was carried out on a diode-array detector covering the wavelengths from 206 to 350 nm. The column was equilibrated with a buffer containing 20% (v/v) of buffer A (acetonitrile) and 80% of buffer B (water containing 0.02% of TFA (trifluoroacetic acid)). A linear gradient is formed from a solution containing 50% of buffer A and 50% of buffer B. After 10 min, the composition of the elution buffer is 25% of buffer A for 75% of buffer B. A new linear gradient is then applied in such a way that, at 30 min, the gradient reaches the value of 100% of buffer B. This value is maintained for 5 minutes in order to clean the column.

2) Analysis by HPLC, Detection by Mass Spectrometry (HPLC/MS):

In the case of an analysis by mass spectrometry, the sample is maintained at 30° C. and the column is maintained at 60° C. during the analysis. The HPLC device used is of the "Alliance HT Waters 2790" type, coupled to a "Waters MicroMass ZQ" mass detector. Unlike the preceding detection method, the elution buffer A does not contain any TFA, but the two buffers A and B contain 0.01% (v/v) of formic acid.

The column was equilibrated with a buffer containing 80% of buffer A' (water containing 0.01% (v/v) of formic acid) and 20% of buffer B' (acetonitrile containing 0.01% (v/v) of formic acid).

The injection begins with a buffer containing 50% of these two buffers. A linear gradient with two ramps is formed from a solution containing 50% of buffer A' and 50% of buffer B'.

After 10 min, the composition of the elution buffer is 25% of buffer A' for 75% of buffer B'. The ramp of the gradient is then modified so as to reach 12.5% of buffer A' and 87.5% of buffer B' after analysis for 25 minutes, and then 100% of buffer B at 30 minutes. This value is maintained for 5 minutes in order to regenerate the column.

The "Waters MicroMass ZQ" mass detector is set for positive electrospray ionization scanning. The values of m/z are between 295 and 450. A "continuum" acquisition mode is selected for the scanning. Moreover, a signal extraction in "SIR" mode is performed in parallel at all the expected masses by natural isotopic abundance for the sterols to be analyzed. The detector is set so as to be able to resolve completely without interference from molecules differing by 1 unit of m/z. All the acquisitions are parametered in such a way that the total acquisition time corresponding to the scanning and to the total time for acquisition of all the SIRs remains less than 2 seconds.

EXAMPLE 8

Culturing of the Yeast Strains for Analysis Of their Sterol Content with or without $^{13}C$ Labeling The strains to be analyzed were cultured in a volume of 50 ml of Kappeli medium (Kappeli et al., 1985) containing 2% of normal D-glucose or of D-glucose-U-$^{13}C_6$ (for the labeling experiments, cf. FIG. 10).

The optical density of the starting culture is 0.1 at 600 nm. This culture is incubated for 72 hours at a temperature of 30° C. with shaking at 200 rpm.

The cells are then recovered by centrifugation of the medium at 600 g for 10 minutes. The cell pellet is then analyzed directly by the analytical techniques presented in example 5 (for the studies not requiring induction with galactose).

However, for the studies of kinetics of induction of the expression of delta 7-reductase and of delta 24-reductase (strains transformed with the plasmid pYES_Delta24 and/or pAG1), the pellet is resuspended in 50 ml of fresh Kappeli medium containing 2% galactose (not labeled with $^{13}C$ carbon).

This culture is incubated at a temperature of 30° C. with shaking at 200 rpm.

Ten ml of culture are recovered after 0 hour, 2 hours, 4 hours, 8 hours and 24 hours of culture.

These culture samples are centrifuged at 800 g for 10 minutes, and the cell pellet is frozen and stored at −20° C. before sterol extraction by the methods described in example 5.

EXAMPLE 9

Identification of the Sterols Present in the Strains Analyzed

The identification of the sterols is based on the combination of the following principles:
Comparison of the behavior by GC, HPLC, GC/MS and HPLC/MS with authentic standards in the case of campesterol (ergosta-5-enol), of ergosterol (ergosta-5,7,22-trienol), of cholesterol (cholesta-5-enol), of desmosterol (cholesta-5,24-dienol), of cholesta-5,22-dienol and of zymosterol (cholesta-8,24-dienol).
Analysis of the absorption spectrum by HPLC and diode-array UV detection (cf. example 7-1)):
This method makes it possible to identify unambiguously, on a spectral basis, five classes of sterols: 1) class SA1: no conjugated diene system, 2) class SA2: presence of a 5,7-diene system; 3) class SA3: presence of a 22,24 (25)-diene system; 4) class SA4: presence of an 8,14-diene system; 5) class SA5: presence of a 22,24(28)-diene system. Classes SA3 and SA5 cannot coexist for structural reasons. Classes SA2 and SA4 cannot coexist for biosynthetic reasons, class SA2 may be combined with structural units of classes SA1, SA3, SA5 so as to form additive composite spectra.
Analysis of the retention times in GC and in HPLC on the basis of an approximate additivity of the retention time shifts associated with each type of unsaturation and with the presence of a backbone of ergosta or cholesta type. Since this criterion is not absolute, it is used as an aid to identification and in order to lift ambiguities, but presents a risk of error if it is used alone. It is therefore only used in combination with the other criteria.
GC/MS analysis (cf. example 6-2)), which provides the molecular mass and a fragmentation profile which can be compared to spectral libraries.
HPLC/electrospray-MS analysis (cf. example 7-2)), which provides, in the case of 3-hydroxysterols, a main signal at the molecular mass −17 (protonation (+ 1) and loss of a water molecule (−18)).
Analysis with all the above systems of the sterol composition of various reference yeast strains disrupted at various points of the biosynthesis.
Analysis of variations in the sterol composition during complementation with various biosynthetic enzymes, and of the kinetics of this complementation during the induction of this complementation.
Analysis of the profile for labeling of the various sterols with the carbon-13 isotope.
Analysis of the UV spectrum of the sterols separated by HPLC at a given retention time. The two 5,7-conjugated double bonds exhibit a typical spectrum with two absorption peaks between 265 and 280 nm, while the two 22,24-conjugated double bonds exhibit an absorption peak at 235 nm. The final, 8,14-conjugated, double bond can be identified by an absorption peak at 245 nm.

EXAMPLE 10

Identification of the Sterols Present in the BMA64 Strain

The BMA64 strain is cultured in a volume of 50 ml of Kappeli medium containing 2% of D-glucose for quantitative and comparative analysis of the sterols.

The optical density of the starting culture is 0.1 at 600 nm. This culture is incubated for 72 hours at a temperature of 30° C. with shaking at 200 rpm.

The cells are then recovered by centrifugation of the medium at 600 g for 10 minutes, and the cell pellet is analyzed by the techniques presented in example 5. The various analyses described made it possible to identify the sterols produced by this strain.

It was thus determined that this strain accumulates more than 80% of its free sterols in the form of ergosterol (ergosta-5,7,22-trienol) (cf. FIG. 8). Two other minor detectable sterols are produced by this strain; they are ergosta-5,7-dienol (substrate for the product of the ERG5 gene) (12%) and zymosterol (ergosta-8,24-dienol) (5%). No trace of cholesterol is detectable (the limit of detection of the method is approximately 0.5% of observable sterols). Small amounts of lanosterol are also detectable (only in the analyses of total sterols).

EXAMPLE 11

Identification of the Sterols Present in the WGIF01 Strain

The WGIF01 strain (cf. example 1) was cultured in a volume of 50 ml of Kappeli medium (Kappeli et al., 1985) containing 2% of D-glucose, for the quantitative and comparative analysis of the sterols.

The optical density of the starting culture is 0.1 at 600 nm. This culture is incubated for 72 hours at a temperature of 30° C. with shaking at 200 rpm.

The cells are then recovered by centrifugation of the medium at 600 g for 10 minutes, and the cell pellet is analyzed by the techniques presented in example 5. The various analyses described made it possible to identify the sterols produced by this strain.

The search, in the chromatogram, for ergosta-5,7,22-trienol (ergosterol) or for ergosta-5,7-dienol is negative (less than 0.5% of the value obtained in BMA64) in HPLC coupled to mass spectrometry. In terms of the free sterols, the strain accumulates 50% of the total zymosterol (cholesta-8,24-dienol), substrate for the product of the ERG6 gene, and 30 and 20%, respectively, of cholesta-5,7,24-trienol and of cholesta-5,7,22,24-tetraenol probably resulting from a mechanism of synthesis identical to that which results in ergosta-5,7-dienol and in ergosta-5,7,22-trienol in the parental strain (cf. FIGS. 3 and 8). This clearly shows that the biosynthetic pathway is blocked at the level of erg6 since the ERG6p enzyme (S-adenosylmethionine delta24 sterol C-methyl-transferase) converts the cholesta-8,24(25)-dienol to ergosta-8,24(28)-dienol (cf. FIG. 2). This accumulation clearly indicates that the WGIF01 strain does not possess a functional copy of the erg 6 gene. The results also indicate that the normal biosynthetic pathway for ergosterol in yeast, and in particular sterol 8,7-isomerase, sterol 5-desaturase and sterol delta 22-desaturase, is capable of converting the cholesta-type substrates with an activity which remains considerable.

EXAMPLE 12

Construction of the WGIF02 Strain and Identification of the Sterols Present in this Strain The WGIF02 strain was obtained by transformation of the WGIF01 strain with the plasmid pYES2 carrying the Δ24-reductase expression cassette (pYES_Delta24, cf. example 3). The clones were selected on a medium lacking uracil and the presence and expression of the Δ24-reductase cDNA is verified by analyzing the sterols of these transformants by means of procedure 1 (cf. example 5-1)).

A clone called WGIF02 was selected since it had a sterol profile that was different from the WGIF01 strain; furthermore, the additional sterol had a retention time similar to that of cholesterol (cf. FIG. 7). The WGIF02 strain is cultured in a volume of 50 ml of Kappeli medium (Kappeli et al., 1985) containing 2% of D-glucose, for the quantitative and comparative analysis of the sterols.

The optical density of the starting culture is 0.1 at 600 nm. This culture is incubated for 72 hours at a temperature of 30° C. with shaking at 200 rpm.

The cells are then recovered by centrifugation of the medium at 600 g for 10 minutes, and the cell pellet is analyzed by the techniques presented in example 5. The various analyses described made it possible to identify the sterols produced by this strain.

The two sterol extract profiles for the WGIF01 strain and for the WGIF02 strain are similar except for the appearance of a new peak identified, by virtue of its mass, its retention time and its conjugated double bonds, as cholesta-5,7,22-trienol (FIGS. 2, 3 and 7). The presence of this compound indicates the expected presence of a 24,25-sterol reductase activity on the double bond in the 24(25)-position of the cholesta-5,7,22,24(25)-tetraenol. In addition, the amount of cholesta-5,7,24-trienol is decreased with the appearance of the cholesta-5,7,22-trienol in the WGIF02 strain (FIGS. 7 and 8). The activity of the enzyme is demonstrated by the conversion of cholesta-5,7,24-trienol representing 30% in the WGIF01 strain and only 12% in WGIF02, the difference, i.e. 18%, being entirely in the form of cholesta-5,7,22-trienol in the WGIF02 strain. This is an unexpected result insofar as the product of conversion of cholesta-5,7,24 by the delta 24-reductase is cholesta-5,7, which is absent in WGIF02, and therefore quantitatively converted to cholesta-5,7,22. This demonstrates another unexpected result, i.e. that cholesta-5,7 is a substrate for sterol 22-desaturase, whereas cholesta-5,7,24 is, according to the sterol profile for the WGIF01 strain, a poor substrate.

EXAMPLE 13

Construction of the WGIF03 Strain and Identification of the Sterols Present in this Strain The WGIF03 strain was obtained by transformation of the WGIF01 strain with the plasmid pAG1. This shuttle plasmid between *E. coli* and *S. cerevisiae* carries an expression cassette for Δ7-reductase, the corresponding cDNA of which is under the control of the GAL10/CYC1 promoter. The WGIF01 strain was transformed by the lithium chloride technique and the transformants were selected on medium containing no adenine. The expression of Delta7-reductase was verified by the appearance, in the sterol profile of the correct clones, of cholesta-5,24(25)-dienol. A clone satisfying these criteria was more particularly selected and called WGIF03.

The WGIF03 strain was cultured in a volume of 50 ml of Kappeli medium (Kappeli et al., 1985) containing 2% of D-glucose, for the quantitative and comparative analysis of the sterols.

The optical density of the starting culture is 0.1 at 600 nm. This culture is incubated for 72 hours at a temperature of 30° C. with shaking at 200 rpm.

The cells are then recovered by centrifugation of the medium at 600 g for 10 minutes, and the cell pellet is analyzed by the techniques presented in example 5. The various analyses described made it possible to identify the sterols produced by this strain.

The expression of the delta7-sterol reductase in the WGIF01 strain (to give the WGIF03 strain), unlike the expression of the delta24-sterol reductase, results in a profound change in the sterol profile of the strain, with a virtually complete disappearance of cholesta-5,7,22,24-tetraenol, cholesta-7,24-dienol and cholesta-8,24-dienol.

This activity is also marked by the appearance of a major peak identified as described previously as cholesta-5,24-dienol or desmosterol. The amounts of cholesta-8,24-dienol change from 12 to 48%. The detected cholesta-5,7,24-trienol changes from 30 to 3% and the detected cholesta-5,7,22,24-tetraenol changes from 23 to 4%, respectively, for the WGIF01 and WGIF03 strains. These observations indicate, unexpectedly, that the sterol delta 7-reductase reduces the cholesta-5,7-dienol in a manner that is virtually independent of the nature of the unsaturations carried by the side chain of the sterols. This result is opposite to that observed with the sterol delta 24-reductase. Unexpectedly, expression of the sterol delta 7-reductase also results in the accumulation (12%) of a molecule that comigrates with the cholesta-5,7-dienol. However, it appears to be relatively unlikely, although not impossible, that this molecule is cholesta-5,7-dieneol, the theoretical level of which should decrease and not increase under these conditions. The appearance of a small amount of cholesta-5,22,24-trienol (8%) is also of interest. The latter sterol is the expected product of the action of sterol 22-desaturase on cholesta-5,24-dienol, the major sterol (60%) in the WGIF03 strain (resulting from the reduction of cholesta-5,7,24-trienol by sterol delta 7-reductase). The small accumulation of cholesta-5,22,24-trienol indicates, unexpectedly, that cholesta-5,24-dienol is not a good substrate for sterol 22-desaturase. By virtue of the results obtained in the WGIF02 strain (cf. example 12), it can be deduced that the presence of an unsaturation in the 24-position (cholesta-5,24-dienol or cholesta-5,7,24-trienol) makes it difficult for the sterol 22-desaturase to metabolize the sterols. The action of the ERG6p enzyme in converting the cholestas unsaturated in the 24-position to ergosta therefore results in the conversion of poor substrates for the ERG5 gene (22-desaturase) to good substrates.

EXAMPLE 14

Construction of the WGIF04 Strain and Identification of the Sterols Present in this Strain The WGIF04 strain was obtained by transformation of the WGIF02 strain with the plasmid pAG1 by the lithium chloride technique, and the transformants were selected on medium containing neither adenine nor uracil. The correct transformants were then confirmed on the basis of the detection of cholesterol accumulation. A clone satisfying these criteria was more particularly selected and called WGIF04. A sample of the WGIF04 strain was deposited with the Collection Nationale de Cultures de Microorganismes (CNCM) [National Collection of Microorganism Cultures], Institut Pasteur, 25, rue du Docteur Roux, 75724 Paris Cedex 15, France, on Apr. 22, 2004 under the registration number I-3203.

Strains that are indistinguishable from WGIF04 can also be obtained by transforming the WGIF03 strain with pYES_Delta24 and applying the same selection.

The WGIF04 strain was cultured in a volume of 50 ml of Kappeli medium containing 2% of D-glucose, for the quantitative and comparative analysis of the sterols.

The optical density of the starting culture is 0.1 at 600 nm. This culture is incubated for 72 hours at a temperature of 30° C. with shaking at 200 rpm.

The cells are then recovered by centrifugation of the medium at 600 g for 10 minutes, and the cell pellet is analyzed by the techniques presented in example 5. The various analyses described made it possible to identify the sterols produced by this strain.

Cholesterol represents 25% of the free sterols of the WGIF04 strain (cf. FIG. 9). The formation of cholesterol in this strain is independently demonstrated in GC and in HPLC, by comigration with an authentic standard and by confirmation both in GC/MS and in HPLC/MS. Cholesterol is undetectable (< 0.5% of total sterols) in all the strains that do not simultaneously express the delta 7-reductase and the delta 24-reductase.

The strains that do not have a disruption in the erg6 gene can produce cholesterol; however this represents less than 5% of the total free sterols. Thus, it was possible to construct the BMA64-pYES_Delta24-pAG1 strain obtained from BMA64 cotransformed with pYES_Delta24 and pAG1. This strain produces cholesterol, the latter representing a few % of the total sterols.

The CA10 strain was transformed with the plasmid pYES_Delta24. This strain also produces cholesterol, the latter representing a few % of the total sterols.

It was possible to demonstrate, moreover, that the formation of cholesterol clearly requires induction of the delta 7-reductase and delta 24-reductase promoters (cf. FIGS. 4 and 5). The strains containing these genes do not produce cholesterol in the absence of induction; FIG. 5 indicates that the maximum level of cholesterol is reached after approximately 24 h of induction. In parallel with the formation of cholesterol (cholesta-5-enol), the formation of cholesta-5,22-dienol is also observed. Analysis of FIG. 4 and of FIG. 5 indicates that the formation of the latter compound occurs more rapidly after induction than the formation of cholesterol, and even begins before induction (cf. FIG. 5A: m/z=367). However, this compound is completely absent if the strain does not carry the two plasmids pAG1 and pYES_Delta24. The formation of 22-dehydrocholesterol is therefore a more rapid process than that of cholesterol formation, but this process involves a precursor which disappears rapidly after induction, leaving room for the formation of cholesterol. The cholesterol can be formed from cholesta-5,24 via the Δ24-reductase or from cholesta-5,7 via the Δ7-reductase. Now, it has been shown that cholesta-5,7-dienol cannot accumulate due to the fact that it is immediately converted to cholesta-5,7,22-trienol. The source of cholesterol is therefore cholesta-5,24-dienol, which is absent at the time of the induction and accumulates at around 4 to 8 hours of induction, before decreasing at around 24 h (FIG. 5). This explains the late appearance of cholesterol since the prior synthesis of cholesta-5,24-dienol is required. Conversely, the two possible precursors for cholesta-5,22-dienol are cholesta-5,7,22-trienol and cholesta-5,22,24-trienol. The latter is absent at the beginning of induction (FIG. 4), whereas the former is present and then rapidly decreases in parallel with the stabilization of the formation of cholesta-5,22-dienol. It may be concluded therefrom that the source of cholesterol is the reduction of the 5,24-dienol by the Δ24-reductase, whereas the formation of cholesta-5,22-dienol results from the reduction of the 5,7,22-trienol by the Δ7-reductase. The formation of cholesta-5,22-dienol by means of the action of Δ22-desaturase on cholesterol is not completely out of the question, but appears to be a minor process on the basis of the preferential accumulation of cholesterol compared to cholesta-5,22-dienol at the long time point (24 h) of the kinetics (FIGS. 4 and 5).

EXAMPLE 15

Optimization of the Biosynthetic Pathway for Cholesterol, Role of Δ22-Desaturase For induction times of the order of 24 h for the WGIF04 strain, the accumulation of cholesta-5,22-dienol represents approximately 50% of that of cholesterol in terms of free sterols (FIG. 4). Disruption of the Δ22-desaturase gene is an option for optimizing cholesterol production. The construction of a strain that is doubly disrupted in terms of Δ22-desaturase (erg5 gene) and of the erg6 gene and that expresses Δ7-reductase and Δ24-reductase is entirely conceivable. A strain carrying the subset: disruption of Δ22-desaturase, expression of Δ7-reductase and expression of Δ24-reductase was produced.

This strain was obtained by transformation of the CA10 strain with the plasmid pYES_Delta24 by the lithium chloride technique and by selection for prototrophy with respect to uracil. The strain obtained was called CA10/Δ24.

The CA10 strain expressing Δ24 sterol reductase produces a relatively small amount of cholesterol (cf. FIGS. 6 and 7) and accumulates mainly ergosta-5-enol and an intermediate amount of ergosta-5,7-dienol. The accumulation of cholesta-5,7-dienol is very low in such a strain, indicating that disruption of the erg6 gene is essential for substantial accumulation of derivatives of the cholesta series. The activity of the Δ24-reductase therefore, surprisingly, competes relatively little with that of the product of the erg6 gene. It may therefore be concluded from these results that the simultaneous disruption of the erg5 and erg6 genes is important for the purpose of optimizing the production of cholesterol.

Disruption of the erg5 gene in the WGIF04 strain would make it possible for those skilled in the art to considerably increase the production of cholesterol. The feasibility of such a strain is established by the construction of the WGIF04 and CA10/Δ24 strains and the fact that this strain is merely an obvious genetic combination to be produced from the two preceding strains. The data derived from WGIF04 indicate that cholesta-5,24 disappears rapidly when Δ24-reductase is expressed (comparing the results obtained with WGIF03 and those obtained with WGIF04). This makes it possible to predict that cholesterol will be synthesized very efficiently in a strain that is simultaneously disrupted for the erg5 and erg6 genes and coexpresses Δ7-reductase and Δ24-reductase, the cholesterol then being the only end sterol.

In conclusion, the minimum requirement for the production of cholesterol at a threshold above or equal to 20% of the total sterols is disruption of the erg6 gene, and expression of the Δ7-reductase and of the Δ24-reductase. Complementary disruption of Δ22-desaturase would make it possible to improve cholesterol productivity and to eliminate the parasitic formation of cholesta-5,22-dienol as end sterol.

EXAMPLE 16

Isotope Labeling of Cholesterol and Definition of Isotope Signatures

The principle of production of a labeled cholesterol is described in FIG. 10. This manipulation first of all consists in growing the yeast on glucose completely labeled with $^{13}$C, for 72 hours of culturing at 30° C.

The cells are then recovered by centrifugation of the medium at 600 g for 10 minutes. The cell pellet is then suspended in 50 ml of fresh Kappeli medium containing 2% of galactose not labeled with $^{13}$C carbon. The cultures are stopped 2 hours, 4 hours, 8 hours or 24 hours after the switch to galactose, and the sterols are extracted and then analyzed (cf. example 7). The switch from glucose to galactose results in induction of the GAL10/CYC1 promoters controlling both the Δ7-reductase gene and the Δ24-reductase gene. Simultaneously, there is a change in isotope labeling of the carbon source. There ensues the de novo synthesis of metabolic intermediates and then of sterol, including cholesterol, comprising a gradual change in labeling. This change in labeling can be characterized by the mass profile of each intermediate sterol. In fact, the incorporation of each $^{13}$C atom induces a shift in mass of one atomic mass unit (AMU). Thus, for example, the cholesterol appears with a molar mass ranging from 386 to 413 daltons depending on the degree of labeling. In analysis by HPLC-mass, using positive electrospray ionization, this corresponds to m/z (mass/charge) values ranging from 369 to 396 (ion M+ H$^+$—H$_2$O, i.e. M+1−18=385−17=369). The sterol retention time in HPLC does not depend detectably on the degree of labeling. The mass spectrum of an HPLC peak corresponding to a single sterol "X" corresponds to a mass distribution which is therefore the superposition (the sum) of the mass distributions for the sterol "X" synthesized at various times after labeling. It is therefore a profile which is complex (FIG. 11), but which can be completely experimentally determined, and which represents a unique isotope signature which depends at the same time:

1) on the labeling protocol and in particular on the culture times and conditions with $^{12}$C glucose and with $^{13}$C galactose,
2) on the precise genetic structure of the strain used,
3) on the precise time at which the cultures are stopped.

This isotope profile has several unique properties:
1) it can be modulated as desired by adjusting the culture conditions, the strain used and the sterol chosen. A unique label register can therefore be produced;
2) it is "combinable", i.e. several isotope signatures corresponding to several unique sterols labeled with isotope profiles that can themselves be modulated can be combined so as to form a "molecular alphabet";
3) it is reproducible and easy to determine experimentally (cf. FIGS. 11 and 12) the double or triple plots which indicate the reproducibility of the profiles;
4) it corresponds to a molecular tracer mixture that is easy to isolate, stable, colorless and odorless, nonvolatile and nontoxic, and that can be incorporated into foods, a medicinal product, additives or other products that can be assimilated by humans;
5) it cannot be falsified without having the specific recombinant strains and the very precise labeling, culturing and extraction conditions. In addition, knowledge of the isotope signature does not make it possible to track back to the parameters which made it possible to produce it.

In summary, an "isotope alphabet" for general use, that cannot be falsified and that can be incorporated into products of any type, including consumables, can be readily obtained by virtue of the present invention. There is a virtually unlimited number of "isotope words" that can be constituted from such an alphabet by making use of both the labeling profiles and the various types of sterols. The incorporation of such signatures into the most varied products therefore constitutes a unique method of labeling that cannot be falsified, unlike, for example, DNA signatures, which can be reproduced once they are known. The signature can, moreover, be read nondestructively, for example by laser ionization followed by mass spectrometry analysis (MALDI-TOF or the like).

EXAMPLE 17

Production of Nonanimal Cholesterol Highly Labeled with $^{13}$C

The use of $^{13}$C galactose or of $^{13}$C ethanol and glucose instead of the unlabeled carbon sources for culturing the WGIF04 strain under the conditions described above for the sterol analyses makes it possible to synthesize very highly labeled sterols, and in particular cholesterol (comprising at least 95% of $^{13}$C carbon). The preparation of $^{14}$C-radioactive sterols and cholesterol is also possible by means of the same approach. The method can also be incorporated into yeast strains that produce steroids, and in particular hydrocortisone (cf. patent application WO 02/061109), in order to produce $^{13}$C-labeled or $^{14}$C-labeled steroids, for example for RIA assays.

EXAMPLE 18

Construction of a Strain that Produces Mainly Cholesterol

The CDR07 Mata strain is described in the patent application published under the number WO 02/061109 and was deposited with the Collection Nationale de Cultures de Microorganismes (CNCM) [National Collection of Microorganism Cultures], rue du Docteur Roux, 75724 Paris Cedex 15, France, according to the provisions of the Treaty of Budapest at the CNCM, on Jan. 24, 2001 under the registration number I-2616.

The CDR07 MATa strain (relevant markers: ade2::GAL10/CYC1$_P$::Δ$^7$; erg5::PGK1$_P$::hygro$^R$; ERG6) was crossed with the WGIF01 strain described in example 1 (relative markers: ERG5; erg6::TRP1).

After sporulation of the diploid, the sterol composition of the spores is determined in order to find spores that produce desmosterol, which is the precursor for cholesterol, as described in example 6. A spore producing desmosterol, having a functional TRP1 gene and carrying the *Arabidopsis thaliana* Δ7-reductase cDNA, as indicated by the PCR analysis, was thus identified. In addition, this strain, called YIM59 is sensitive to hygromycin, indicating that the ERG5 gene is functional.

A sterol preparation, prepared as described in examples 6 and 9, showed that this YIM59 strain produces sterols that have the same retention time as zymosterol and desmosterol. The YIM59 strain also showed auxotrophies for adenine, leucine, uracil and histidine. The presence of desmosterol demonstrates that this strain expresses the sterol Δ7 reductase and that it carries a nonfunctional erg6 allele.

With the aim of improving the level of expression of human DHCR24, the nucleotide sequence of the DHCR24 cDNA was modified; in order to improve the translation at the initiating ATG, the promoter controlling the expression of DHCR24 was also modified. The new promoter selected is the CYC1 promoter of cytochrome cl, as a replacement for the GAL1 inducible promoter of the plasmid pYES_Delta24 (cf. example 3).

The sequence corresponding to the terminal NH2 of the DHCR24 reductase as a fusion with the CYC1 promoter was modified as follows:

(SEQ ID No. 7)
tagcgtggatggccaggcaactttagtgctgacacatacaggcatatata tatgtgtgcgacgacacatgatcatatggcatgcatgtgctctgtatgta tataaaactcttgttttcttcttttctctaaatattctttccttatacat taggtcctttgtagcataaattactatacttctatagacacgcaaacaca aaggaattgacaagtttgtacaaaaaagcaggctaaaaaATGGAACCTGC

CGTGTCGCTGGCCGTGTGCG.

The small letters represent the partial nucleotide sequence of the CYC1 promoter followed by the AttB1 recombination sequences and then an AAAA sequence which precedes the initiating ATG. The sequence of the first two codons was also modified (sequence GAA-CCT after the ATG initiating codon).

The final plasmid carrying the DHCR24 cDNA under the control of the CYC1 promoter and also the S. cerevisiae 2μ origin of replication and the URA3-d selection marker was called pIM331. Its equivalent without the DHCR24 cDNA was called pIM303.

The YIM59 strain is transformed independently with the plasmids pIM303 and pIM331, and two transformants carrying the plasmid pIM303 (YIM59/pIM303 strain) or pIM331 (YIM59/pIM331 strain) are more particularly selected.

These strains are cultured in a reconstituted rich medium of the Kappeli type for 72 hours at 28° C. in order to attain an absorbance of 40 at 600 nm. Total sterol extracts (esterified sterols and free sterols) of the YIM59/pIM303 strain (not carrying the DHCR24 cDNA) and of the YIM59/pIM331 strain (carrying the DHCR24 cDNA) are produced in the presence of methanolic potassium hydroxide (cf. examples 5 and 6). These two strains are tested for their ability to produce cholesterol. Some of the results (GC) are given in FIG. 13. The retention times presented are given in minutes on two chromatograms.

It was thus possible to show that the strain that does not carry the vector for expression of DHCR24 (YIM59/pIM303 strain) does not produce cholesterol (part A), but mainly desmosterol (part A). Conversely, the strain that carries the DHCR24 cDNA (YIM59/pIM331 strain) produces a sterol that has the retention time of cholesterol (part B). It was possible to demonstrate, by techniques of gas chromatography coupled to electron-impact mass spectrometry (as described in example 6), that this sterol is indeed cholesterol. Using the surface areas of each of the sterol peaks, it was possible to estimate that the amount of cholesterol produced by the YIM59/pIM331 strain was 57% of the sterols.

Depositing of Biological Material

The following organisms were deposited, on Apr. 22, 2004, with the Collection Nationale de Cultures de Microorganismes (CNCM) [National Collection of Microorganism Cultures], 25 rue du Docteur Roux, 75724 Paris Cedex 15, France, according to the provisions of the Treaty of Budapest.

WGIF04 strain deposited under the registration number I-3203.

All the publications and patents mentioned are incorporated into the present application by way of reference.

BIBLIOGRAPHY

Adams, A. K., and C. Holm. 1996. Mol Cell Biol. 16:4614-20.
Ausubel Fred M., Brent Roger, Kingston Robert E., Moore David D., Seidman J. G., Smith John A., Struhl Kevin (Editors). Current Protocols in Molecular Biology, published by John Wiley & Sons Inc. Current Protocols Customer Service, 605 Third Avenue, 9th Floor New York, N.Y. 10158 USA (publication updated March 2002).
Baudin-Baillieu, A., E. Guillemet, C. Cullin, and F. Lacroute. 1997. Yeast. 13:353-6.
Bonneaud, N., O. Ozier-Kalogeropoulos, G. Y. Li, M. Labouesse, L. Minvielle-Sebastia, and F. Lacroute. 1991. Yeast. 7:609-15.
Bowman, S. et al. 1997. Nature. 387:90-3.
Duport, C., B. Schoepp, E. Chatelain, R. Spagnoli, B. Dumas, and D. Pompon. 2003. Eur J Biochem. 270:1502-14.
Gietz, R. D., R. H. Schiestl, A. R. Willems, and R. A. Woods. 1995. Yeast. 11:355-60.
Goffeau, A., et al. 1996. Science. 274:546, 563-7.
Jensen-Pergakes, K. L., M. A. Kennedy, N. D. Lees, R. Barbuch, C. Koegel, and M. Bard. 1998. Antimicrob Agents Chemother. 42:1160-7.
Kaneshiro, E. S., J. A. Rosenfeld, M. Basselin-Eiweida, J. R. Stringer, S. P. Keely, A. G. Smulian, and J. L. Giner. 2002. Mol. Microbiol. 44:989-99.
Kappeli, O., M. Arreguin, and M. Rieger. 1985. J Gen Microbiol. 131:1411-6.
Kelly, S. L., D. C. Lamb, B. C. Baldwin, A. J. Corran, and D. E. Kelly. 1997. J Biol Chem. 272:9986-8.
Lecain, E., X. Chenivesse, R. Spagnoli, and D. Pompon. 1996. J Biol Chem. 271:10866-73.
McCammon, M. T., M. A. Hartmann, C. D. Bottema, and L. W. Parks. 1984. J Bacteriol. 157:475-83.
Moebius, F. F., B. U. Fitzky, J. N. Lee, Y. K. Paik, and H. Glossmann. 1998. Proc Natl Acad Sci USA. 95:1899-902.
Noda, H., and Y. Koizumi. 2003. Insect Biochem Mol Biol. 33:649-58.
Ozier-Kalogeropoulos, O., A. Malpertuy, J. Boyer, F. Tekaia, and B. Dujon. 1998. Nucleic Acids Res. 26:5511-24.
Skaggs, B. A., J. F. Alexander, C. A. Pierson, K. S. Schweitzer, K. T. Chun, C. Koegel, R. Barbuch, and M. Bard. 1996. Gene. 169:105-9.
Sturley, S. L. 2000. Biochim Biophys Acta. 1529:155-63.
Szczebara, F. M., et al. 2003. Nat Biotechnol. 21:143-9.
Tait, E., M. C. Simon, S. King, A. J. Brown, N. A. Gow, and D. J. Shaw. 1997. Fungal Genet Biol. 21:308-14.
Taton, M., and A. Rahier. 1991. Biochem Biophys Res Commun. 181:465-73.
Taylor, F. R., and L. W. Parks. 1978. J Bacteriol. 136:531-7.
Waterham, H. R., J. Koster, G. J. Romeijn, R. C. Hennekam, P. Vreken, H. C. Andersson, D. R. FitzPatrick, R. I. Kelley, and R. J. Wanders. 2001. Am J Hum Genet. 69:685-94.
Wood, V., et al. 2002. Nature. 415:871-80.

TABLE 1

Evaluation of the spectral contributions of the sterol unsaturations (extinction coefficients mM$^{-1}$ cm$^{-1}$)

| Unsaturation | Wavelength (nm) | | |
|---|---|---|---|
|  | 206 | 235 | 280 |
| 5 | 3.9 | 0.0 | 0.0 |
| 5, 7 | 4.0 | 1.7 | 11.5 |
| 5, 7, 22 | 4.8 | 1.7 | 11.5 |
| 5, 22 | 4.4 | 0.0 | 0.0 |
| 5, 24 | 6.9 | 0.0 | 0.0 |
| 5, 22, 24 | 8.7 | 27.0 | 0.0 |
| 5, 7, 24 | 7.5 | 1.7 | 11.5 |
| 5, 7, 22, 24 | 9.2 | 29.8 | 11.5 |
| 8, 24 | 6.9 | 0.0 | 0.0 |

The invention claimed is:

1. An isolated organism of the kingdom Fungi comprising enzyme expression of at least one of the enzymes selected from the group consisting of 7-dehydrocholesterol reductase and 3β-hydroxysterol Δ24-reductase, wherein said enzyme expression is obtained by transformation of the organism, and enzyme inactivation of at least one of the enzymes selected from the group consisting of C-22 sterol desaturase and sterol 24-C-methyltransferase.

2. The isolated organism of claim 1, wherein said enzyme inactivation is carried out by gene inactivation.

3. The isolated organism of claim 1, wherein the organism is chosen from the genus *Saccharomyces* or *Schizosaccharomyces*.

4. A *Saccharomyces cerevisiae* yeast strain characterized in that it is the WGIF04 strain deposited with the Collection Nationale de Cultures de Microorganismes (CNCM) [National Collection of Microorganism Cultures] on Apr. 22, 2004 under the registration number I-3203.

5. A method for producing cholesterol of non-animal origin comprising culturing the isolated organism of claim 1.

6. The method of claim 5, further comprising extracting the cholesterol after culturing of the organism.

7. The method of claim 6, wherein the extraction of the cholesterol is carried out with a non-water-miscible solvent.

8. The method in of claim 6 or 7, wherein a saponification step is carried out before the extraction of the cholesterol.

9. The method of claim 8, wherein a step comprising mechanical grinding of the organisms is carried out before the saponification or the extraction of the cholesterol.

10. A method for producing cholesterol, or one of its metabolic intermediates, or a mixture of sterols, labeled with $^{13}C$ or with $^{14}C$, comprising:

a) culturing the isolated organism of claim 1 on a $^{13}C$-labeled or $^{14}C$-labeled substrate, and
b) extracting said cholesterol, or one of its metabolic intermediates, or the mixture of sterols.

11. A method for producing an isotopic mixture, wherein the isotopic mixture is selected from the group consisting of cholesterol, cholesterol intermediates, and cholesterol metabolites, labeled at various positions using isotope labels, comprising:

a) culturing the isolated organism of claim 1 on a labeled substrate, and
b) removing the organism from the labeled substrate onto an unlabeled substrate, wherein the culture times on the labeled substrate and the unlabeled substrate produces the isotopic mixture of cholesterol, of cholesterol intermediates, or of cholesterol metabolites.

12. The isolated organism of claim 1, wherein 7-dehydrocholesterol reductase is expressed.

13. The isolated organism of claim 1, wherein 3β-hydroxysterol Δ24-reductase is expressed.

14. The isolated organism of claim 1, wherein 7-dehydrocholesterol reductase and 3β-hydroxysterol Δ24-reductase are expressed.

15. The isolated organism of claim 1, wherein C-22 sterol desaturase is inactivated.

16. The isolated organism of claim 1, wherein sterol 24-C-methyltransferase is inactivated.

17. The isolated organism of claim 1, wherein C-22 sterol desaturase and sterol 24-C-methyltransferase are inactivated.

* * * * *